(12) United States Patent
Akhavan-Tafti et al.

(10) Patent No.: US 7,247,726 B2
(45) Date of Patent: *Jul. 24, 2007

(54) COMPOUNDS FOR GENERATING CHEMILUMINESCENCE WITH A PEROXIDASE

(75) Inventors: Hashem Akhavan-Tafti, Howell, MI (US); Renuka de Silva, Northville, MI (US); Wenhua Xie, Novi, MI (US)

(73) Assignee: Lumigen, Inc., Southfield, MI (US)

( * ) Notice: Subject to any disclaimer, the term of this patent is extended or adjusted under 35 U.S.C. 154(b) by 202 days.

This patent is subject to a terminal disclaimer.

(21) Appl. No.: 10/468,257

(22) PCT Filed: Dec. 18, 2002

(86) PCT No.: PCT/US02/37611

§ 371 (c)(1),
(2), (4) Date: Apr. 15, 2004

(87) PCT Pub. No.: WO03/053934

PCT Pub. Date: Jul. 3, 2003

(65) Prior Publication Data

US 2004/0176599 A1    Sep. 9, 2004

Related U.S. Application Data

(63) Continuation-in-part of application No. 10/205,050, filed on Jul. 25, 2002, now Pat. No. 6,858,733, and a continuation-in-part of application No. 10/029,222, filed on Dec. 20, 2001, now Pat. No. 6,872,828.

(51) Int. Cl.
  *C02F 9/06* (2006.01)
  *C07D 219/02* (2006.01)

(52) U.S. Cl. .......................... 546/23; 546/79; 252/700; 435/4; 435/25; 435/28; 435/968

(58) Field of Classification Search ................. 546/23, 546/79; 514/290
See application file for complete search history.

(56) References Cited

U.S. PATENT DOCUMENTS 6,126,870 A    10/2000  Akhavan-Tafti
6,872,828 B2 *  3/2005  Akhavan-Tafti et al. ...... 546/23

OTHER PUBLICATIONS

Akiba et al Synthesis of 1,4-dithiaful venes and 1,4-dithiafulvalences by carbonyl olefination using 2-dinethoxyphosphinyl-1,3-benzodithiole. Bulletin of the Chemical Society of Japan. 1978, vol. 51, No. 9, pp. 2674-2683, especially p. 2677, compounds of 6c and 6d.

* cited by examiner

*Primary Examiner*—Rita Desai
(74) *Attorney, Agent, or Firm*—Richard S. Handley

(57) ABSTRACT

Novel compounds comprising a C—C double bond substituted at one carbon with two sulfur atom-containing groups are disclosed. The compounds are useful in methods and compositions for generating chemiluminescence rapidly by reaction with a peroxidase enzyme and a peroxide. The chemiluminescence thus produced can be used as a detectable signal in assays for peroxidase enzymes or peroxide-producing enzymes and in assays employing enzyme-labeled specific binding pairs.

3 Claims, 8 Drawing Sheets

Ref. 1

5000 1000 180 30 5

Compound 1

5000 1000 180 30 5

Compound 27  Compound 37

5000 1000 180 30 5    5000 1000 180 30 5

COMPOUNDS FOR GENERATING CHEMILUMINESCENCE WITH A PEROXIDASE

CROSS REFERENCE TO RELATED APPLICATION

This application is a continuation-in-part of applicant's co-pending U.S. application Ser. No. 10/029,222 filed on Dec. 20, 2001 now U.S. Pat. No. 6,872,828 and Ser. No. 10/205,050 filed on Jul. 25, 2002 now U.S. Pat. No. 6,858,733.

FIELD OF THE INVENTION

The present invention relates to chemiluminescent compounds and compositions which react with a peroxidase and a peroxide to generate chemiluminescence. In particular, the present invention relates to improved compositions containing novel ketene dithioacetal compounds which react with a peroxidase and a peroxide to produce visible chemiluminescence. The invention further relates to assay methods for detecting a peroxidase and for detecting peroxidase-labeled specific binding partners in immunoassays, nucleic acid probe assays and other specific binding pair assays.

BACKGROUND OF THE INVENTION

Peroxidase enzymes such as horseradish peroxidase (HRP) are frequently used as markers or labels in enzyme-linked assays for biological molecules and other analytes of interest such as drugs, hormones, steroids and cancer markers. Chemiluminescent detection of these enzymes offers a safe, convenient and sensitive means of measuring the amount of enzyme in a sample or the amount of an enzyme-labeled analyte or labeled specific binding partner for an analyte. Other chemiluminescent reaction schemes have been developed to quantify the level of particular peroxidase enzymes.

a. Chemiluminescent Peroxidase Substrates. Amino-substituted cyclic acylhydrazides such as the well-known luminol and isoluminol react with $H_2O_2$ and a peroxidase catalyst (such as horseradish peroxidase, HRP) under basic conditions with emission of light. This reaction has been used as the basis for analytical methods for the detection of $H_2O_2$ and for the peroxidase. Heterocyclic analogs of luminol such as 8-amino-5-chloro-7-phenylpyrido[3,4-d-pyridazine-1,4 (2H,3H)dione (M. Ii, et al., Biochem. Biophys. Res. Comm., 193(2), 540-5 (1993)); pyridazinoquinoxalinones (U.S. Pat. No. 5,324,835) and 1,3-disubstituted pyrazolo[4',3':5',6']pyrido-[2,3-d]-pyrazinediones (Y. Tominaga, et al., Tetrahedron Lett., 36, 8641-4 (1995)) are known to react with a peroxidase and peroxide to produce chemiluminescence. Other hydrazide compounds which are chemiluminescent when oxidized by a peroxidase and a peroxide are hydroxy-substituted phthalhydrazides (U.S. Pat. No. 5,552,298).

Applicant's U.S. Pat. Nos. 5,491,072, 5,523,212 and 5,593,845 disclose chemiluminescent N-alkylacridan-carboxylic acid esters, thioesters and sulfonimides which produce light upon reaction with a peroxide and a peroxidase for use in detecting peroxidases and in assays. A PCT application (WO 94/02486) describes the chemiluminescent reaction of spiroacridan compounds with hydrogen peroxide. The reaction is enhanced by the addition of horseradish peroxidase.

Various compounds of biological origin, collectively termed luciferins, are oxidized by a peroxidase (summarized in L. J Kricka and G. H. G. Thorpe, in Luminescence Immunoassay and Molecular Applications, K. Van Dyke and R. Van Dyke, eds., CRC Press, Boca Raton, 1990, pp. 77-98). When hydrogen peroxide is not utilized, the enzyme is functioning as an oxidase.

Certain phenol compounds produce chemiluminescence on oxidation with a peroxidase. As examples, pyrogallol B-1 and purpurogallin B-2 are cited in Kricka and Thorpe, ibid. as well as the coumarin-type compounds coumarin, umbelliferone and esculin (D. Slawinska, J. Slowinski, J. Biolumin. Chemilumin., 4, 226-30 (1989)); phloroglucinol B-3 (M. Halmann, et al., Photochem. Photobiol., 30, 165-7 (1979)); and acetaminophen B-4 (K. Schmitt, G. Cilento, Photochem. Photobiol., 51, 719-23 (1990)).

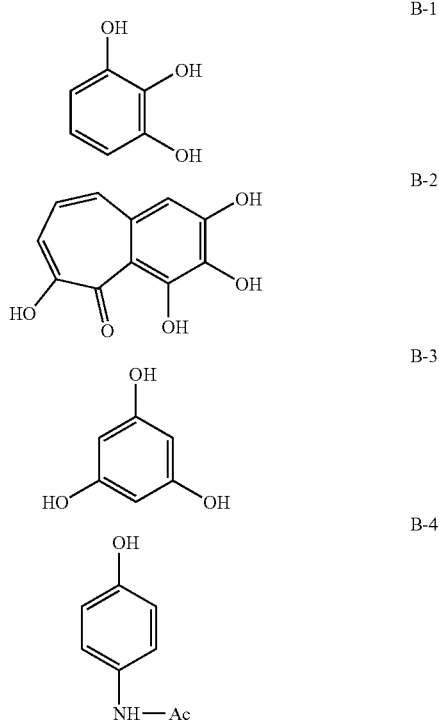

Other miscellaneous compounds reported to produce weak chemiluminescence in the presence of a oxygen or peroxide and a peroxidase are a synthetic Schiff base-containing polymer ((R. Zoulik, et al., Coll. Czech. Chem. Commun., 60, 95-103 (1995)); indole-3-acetic acid in the presence of xanthene dyes with or without hydrogen peroxide (S. Krylov, A. Chebotareva, FEBS, 324(1), 6-8 (1993); tyrosine, tryptophan and chlorpromazine (M. Nakano, J. Biolumin. Chemilumin. 4, 231-40 (1989)) and MCLA B-8 M. (Mitani, et al., J. Biolumin. Chemilumin. 9, 355-61 (1994)) which have the respective structures B-5-B-8 as shown below.

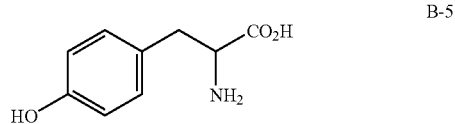

-continued

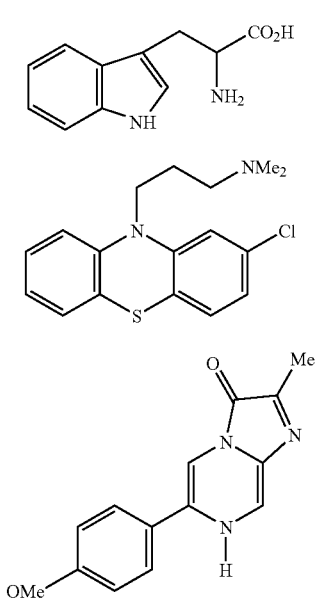

B-6

B-7

B-8

None of the foregoing references disclose the chemiluminescent oxidation of the presently disclosed compounds by a peroxidase b. Reaction of Enols with HRP. A series of papers describe the peroxidase-catalyzed air oxidation of enolizable aldehydes (H. Gallardo, et al., Biochim. Biophys. Acta, 789, 57-62 (1984); W. J. Baader, et al., Biochem. Ed., 14(4), 190-2 (1986); I. Nantes, et al., Photochem. Photobiol., 63(6), 702-8 (1996)). The reactive substrate is thought to be the small quantity of the enol form in equilibrium with the aldehyde. The reaction of the aldehyde is catalyzed by enol phosphates, but the enol phosphate itself is not consumed. The reference teaches that the enol phosphate does not react with a peroxidase to produce chemiluminescence. Energy transfer to fluorescent energy acceptors increased light emission (M. T. Grijalba, et al., Photochem. Photobiol., 63(6), 697-701 (1996)). Aldehydes masked as enol silyl ethers (Baader, ibid.) or enol acetates were used in coupled assays in which the enol was unmasked in a first step to generate an enol in situ which subsequently reacted with a peroxidase to generate chemiluminescence (A. Campa, et al., Photochem. Photobiol., 63(6), 742-5 (1996)).

c. Peroxidase Enhancers. Numerous enhancers have been employed in order to increase the quantity and duration of chemiluminescence from the reaction of a peroxidases with known chemiluminescent substrates including the aforementioned luminol and the acridancarboxylic acid derivatives. These include benzothiazole derivatives such as D-luciferin, various phenolic compounds such as p-iodophenol, p-phenylphenol, naphthols and aromatic amines as listed in G. Thorpe, L. Kricka, in Bioluminescence and Chemiluminescence, New Perspectives, J. Scholmerich, et al, Eds., pp. 199-208 (1987). Other compounds which function as enhancers of the chemiluminescent oxidation of amino-substituted cyclic acylhydrazides by a peroxidase include 4-(4-hydroxyphenyl)-thiazole (M. Ii, ibid.), a group of compounds disclosed in U.S. Pat. No. 5,171,668, 2-hydroxy-9-fluorenone, and a group of hydroxy-substituted benzoxazole derivatives as disclosed in U.S. Pat. No. 5,206,149 and certain phenylboronic acid compounds as described in U.S. Pat. No. 5,629,168. None of the foregoing references disclose the chemiluminescent oxidation of the present compounds by a peroxidase alone or with the use of enhancers.

d. Enhancement of Chemiluminescent Peroxidase Reactions by Surfactants. Enhancement of the chemiluminescence produced in peroxidase-catalyzed reactions using polymeric and monomeric surfactants is known in the art. Enhancement can occur by affecting the outcome of one or more steps e.g. by increasing the fluorescence quantum yield of the emitter, by increasing the percentage of product molecules produced in the excited state, by increasing the fraction of molecules undergoing the chemiluminescent reaction through inhibition of competing side reactions or by promoting the action of an enzyme catalyst. No clear or consistent pattern exists concerning the effect of polymeric and monomeric surfactants on chemiluminescent reactions. It is impossible to predict which surfactant compounds, if any, may enhance the chemiluminescence from a particular process and can only be determined by substantial experimentation.

The cationic polymeric surfactant poly-N-ethyl-4-vinylpyridinium bromide completely inhibited the chemiluminescent reaction of luminol by a negatively charged insulin-peroxidase conjugate and diminished chemiluminescence to a lesser extent when the native enzyme was used (S. B. Vlasenko, et al., J. Biolumin. Chemilumin., 4, 164-176 (1989)).

A published Japanese Patent Application No. JP 06,242, 111 and a paper (R. Iwata, et al., Anal. Biochem., 231, 170-4 (1995)) disclose the use of nonionic surfactant and skim milk in the chemiluminescent peroxidation of luminol to lower background emission or enhance signal/noise.

None of the foregoing references disclose the chemiluminescent oxidation of the present compounds by a peroxidase or chemiluminescence enhancement with surfactants.

e. Assays using HRP. The enzyme horseradish peroxidase has found widespread use in enzyme immunoassays and DNA hybridization assays with chemiluminescent detection using luminol or isoluminol as substrate. Commercially available kits using HRP conjugates and enhanced luminol chemiluminescent detection are available. Chemiluminescent peroxidase assays are also disclosed in the aforementioned U.S. Pat. Nos. 5,491,072, 5,523,212 and 5,593,845. No references disclose the chemiluminescent peroxidase assays using the present compounds as the substrates.

f. New Chemiluminescent Peroxidase Substrates. A new class of chemiluminescent peroxidase substrates was disclosed by Applicants in their previous U.S. Pat. No. 5,922, 558, and published PCT Application No. WO99/14220. The disclosure of these applications is fully incorporated herein. While the disclosure of these publications describes a class of heterocyclic compounds generic of the compounds of the present invention, the present compounds are unexpectedly superior in producing light from reaction with a peroxidase enzyme and a source of peroxide.

g. Benzodithiafulvalenes. Synthesis of a benzodithiafulvalene having the structure below has been described. (K. Akiba, K. Ishikawa, N. Inamoto, Synthesis, 12, 861-2 (1977). No information concerning its ability to function as a chemiluminescent peroxidase substrate is known.

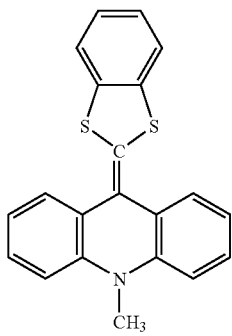

SUMMARY OF THE INVENTION

It is an object of the present invention to provide improved compositions containing compounds which react with a peroxidase and a peroxide to provide chemiluminescence and for detection of the peroxidase.

It is a particular object of the present invention to provide improved compounds and compositions containing them wherein the improved compounds have the formula:

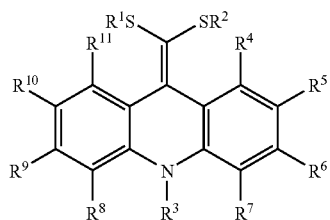

containing a carbon-carbon double bond substituted at one terminus of the double bond with two sulfur atoms each attached to another group $R^1$ or $R^2$ and the other terminus of the double bond forming a portion of a polycyclic heterocyclic ring system containing a nitrogen atom.

Compositions containing the compounds of the invention preferably incorporate enhancer compounds for promoting the chemiluminescence produced on reaction of compounds of the present invention with a peroxidase and improving the analytical utility of the invention.

It is a further object of the present invention to provide methods for rapidly generating chemiluminescence upon reaction with a peroxidase and a peroxide employing the present compounds and compositions.

It is yet another object of the present invention to provide chemiluminescent compositions and methods for use in detecting peroxidases and conjugates in immunoassays, nucleic acid probe assays, western blot assays, Southern blot assays and other assays by generally known methods which employ enzyme labels for detection of analytes. The assays are thus useful for detecting analytes in such assays by detecting the peroxidase or conjugate and relating the chemiluminescence produced thereby to the presence or amount of the analyte.

DESCRIPTION OF THE PREFERRED EMBODIMENTS

Figure 1:
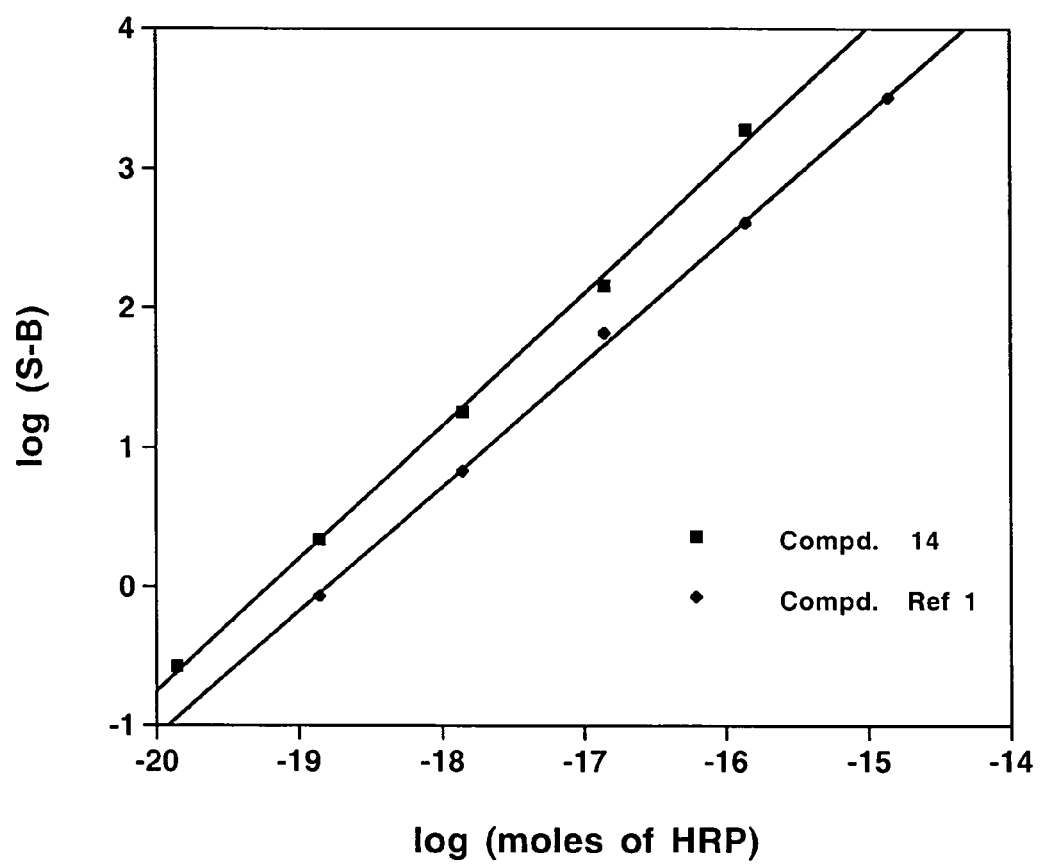
FIG. 1 is a graph relating the amount of HRP to the chemiluminescence intensity at 1.5 min emitted by 100 μL of a reagent described in Example 7 containing compound 14 triggered at room temperature. Chemiluminescence emission was initiated by addition of 100 μL of the reagent to 10 μL of solutions of HRP containing between $1.4\times10^{-16}$ and $1.4\times10^{-20}$ moles of enzyme in the wells of a white microplate. The term S-B refers to the chemiluminescence signal (S) in Relative Light Units (RLU) in the presence of HRP corrected for background chemiluminescence (B) in the absence of HRP. For comparison, the relationship between S-B and amount of HRP is also shown for reference compound 1 measured at 15 min.

Definitions:

Alkyl—A branched, straight chain or cyclic hydrocarbon group containing from 1-20 carbons. Lower alkyl as used herein refers to those alkyl groups containing up to about 8 carbons.

Alkylene—A divalent alkyl chain group.

Alkenyl—A branched, straight chain or cyclic hydrocarbon group containing at least one C—C double bond and containing from 2-20 carbons. Lower alkenyl as used herein refers to those alkenyl groups containing up to about 8 carbons.

Alkynyl—A branched or straight chain hydrocarbon group containing at least one C—C triple bond and containing from 2-20 carbons. Lower alkynyl as used herein refers to those alkynyl groups containing up to about 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include oxidase enzymes and peroxidase enzymes.

Aryl—An aromatic ring-containing group containing 1 to 5 carbocyclic aromatic rings, which can be substituted with 1 or more substituents other than H.

Halogen—Fluorine, chlorine, bromine or iodine atoms.

Heteroalkyl—A monovalent alkyl chain group in which at least one of the nonterminal carbon atoms is replaced by a nitrogen, oxygen or sulfur atom.

Heteroalkylene—A divalent alkylene chain group in which at least one of the nonterminal carbon atoms is replaced by a nitrogen, oxygen or sulfur atom.

Luminescent—capable of emitting light when excited to an electronic excited state. The light can be emitted either as fluorescence when decaying from a singlet excited state or as phosphorescence when decaying from a triplet excited state.

Peroxide—A compound containing an O—O bond, preferably hydrogen peroxide or a complex of hydrogen peroxide such as urea peroxide, perborate or percarbonate.

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

Substituted—Refers to the replacement of at least one hydrogen atom on a group by a non-hydrogen group. It should be noted that in references to substituted groups it is intended that multiple points of substitution can be present unless clearly indicated otherwise.

It has been discovered that compounds of formula I below react with a peroxide and a peroxidase to generate chemiluminescence with unexpectedly superior properties. Ketene dithioacetal compounds of the present invention have the formula I:

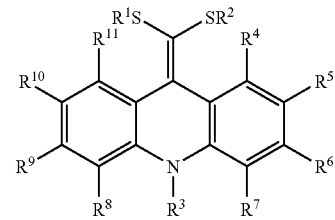

wherein $R^1$ and $R^2$ are each organic groups containing from 1 to about 50 non-hydrogen atoms in addition to the necessary number of H atoms required to satisfy the valencies of the atoms in the group and wherein $R^1$ and $R^2$ can be joined together to form a ring. The groups $R^1$ and $R^2$ can contain from 1 to about 50 non-hydrogen atoms selected from C, N, O, S, P, Si and halogen atoms but more preferably from 1 to about 20 such atoms. Preferred groups for $R^1$ and $R^2$ include alkyl, substituted alkyl, aryl, substituted aryl, aralkyl and substituted aralkyl groups. More preferred are alkyl, substituted alkyl, aryl, and substituted aryl. Substituent groups other than H atoms, such as ionic groups or polar groups, can be incorporated in various numbers and at selected positions on the carbon chain or ring in order to modify the properties of the compound or to provide for convenience of synthesis. Such properties include, for example, chemiluminescence quantum yield, rate of reaction with the enzyme, maximum intensity of light emission, duration of light emission, wavelength of light emission, solubility in the reaction medium. Preferred groups conferring water solubility are sulfonate salt groups —$SO_3^-$, sulfate salt groups —$OSO_3^-$, phosphonate salt groups —$PO_3^-$, phosphate salt groups —$OPO_3^{-2}$, carboxylate salt groups —$COO^-$ and ammonium salt groups—$NR_3^+$ and phosphonium salt groups —$PR_3^+$. One or more groups which permit covalent coupling to another molecule such as a specific binding partner can also be included as substituents on $R^1$ and $R^2$. Exemplary specific substituents include, without limitation, alkoxy, aryloxy, hydroxy, halogen, amino, substituted amino, carboxyl, carboalkoxy, carboxamide, cyano, and sulfonate groups.

When $R^1$ and $R^2$ are joined together to form a ring, the ring is preferably from 5 to 30 atoms and is comprised of additional carbon and/or oxygen atoms selected from alkylene chains, heteroalkylene chains and unsaturated chains containing double bonds. The carbon atoms in the chain can be substituted with non-hydrogen atoms as described above in connection with groups $R^1$ and $R^2$. Preferred ring sizes are from five to seven atoms.

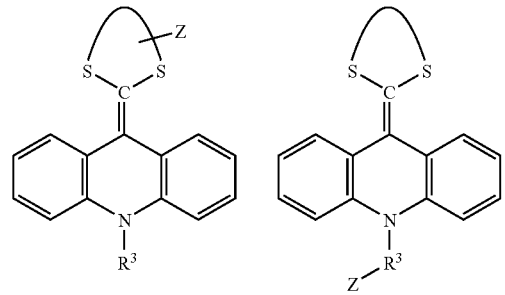

-continued

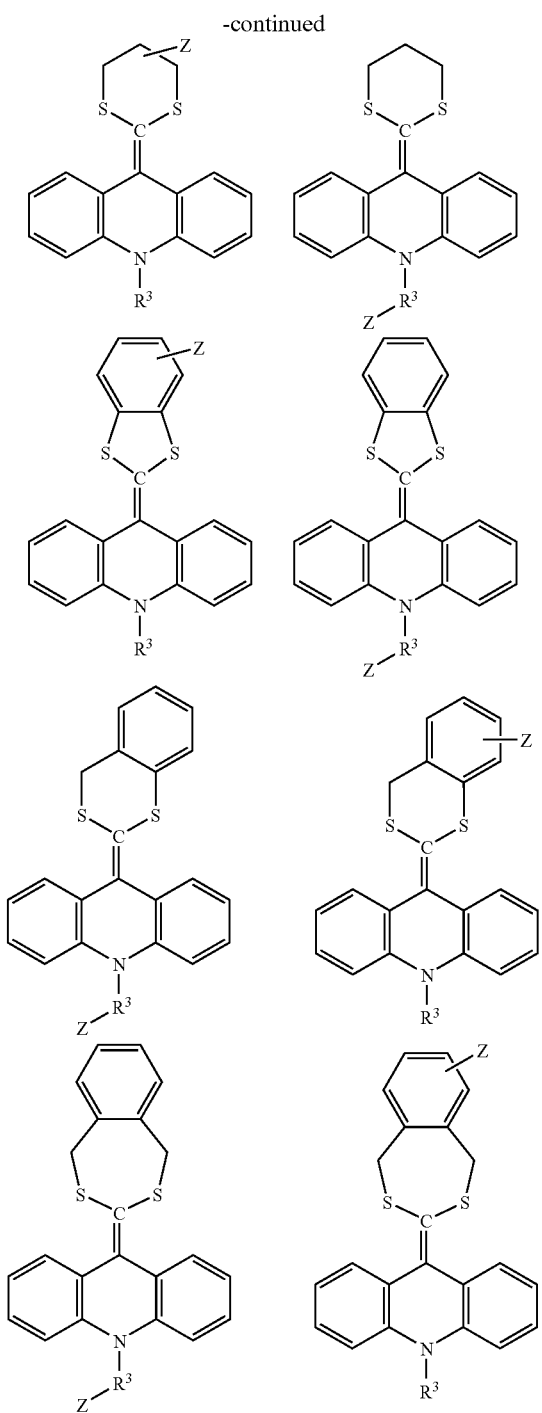

In a preferred embodiment $R^1$ and $R^2$ are joined to complete a six-membered ring which is substituted on the ring with at least one water-solubility conferring group Z as described above. In another embodiment the Z group is attached instead to the group $R^3$. The ring formed by linking $R^1$ and $R^2$ can also be a five to seven membered ring fused to a second ring such as a benzo-fused ring. Likewise it is preferred that at least one water-solubility conferring Z group is substituted on one of the fused rings or on the group $R^3$. Exemplary structures are shown above.

In the present compounds, the group $R^3$ is an organic group containing from 1 to 50 non-hydrogen atoms selected from C, N, O, S, P, Si and halogen atoms in addition to the necessary number of H atoms required satisfy the valencies of the atoms in the group. More preferably $R^3$ contains from 1 to 20 non-hydrogen atoms. The organic group is preferably selected from the group consisting of alkyl, substituted alkyl, aryl, substituted aryl, aralkyl and substituted aralkyl groups. More preferred groups for $R^3$ include substituted or unsubstituted $C_1$-$C_4$ alkyl groups, substituted or unsubstituted phenyl or naphthyl groups, and substituted or unsubstituted benzyl groups. When substituted, exemplary substituents include, without limitation, alkoxy, aryloxy, hydroxy, halogen, amino, substituted amino, carboxyl, carboalkoxy, carboxamide, cyano, sulfonate and phosphate groups. One preferred $R^3$ group is an alkyl or heteroalkyl group substituted with at least one water-solubility conferring group.

Substituent groups can be incorporated in various quantities and at selected ring or chain positions in the heterocyclic ring in order to modify the properties of the compound or to provide for convenience of synthesis of the final compound. Such properties include, without limitation, chemiluminescence quantum yield, rate of reaction with the enzyme, maximum light intensity, duration of light emission, wavelength of light emission and solubility in the reaction medium. The groups $R^4$ to $R^{11}$, which can be the same or different, each are a substituent which can contain from 1 to 50 atoms selected from C, H, N, O, S, P, Si and halogen atoms and which permit the light to be produced and can include, without limitation, alkyl, substituted alkyl, aryl, substituted aryl, aralkyl, alkenyl, alkynyl, alkoxy, aryloxy, halogen, amino, substituted amino groups, carboxyl, carboalkoxy, carboxamide, cyano, sulfonate and phosphate groups. It is preferred that $R^4$ to $R^{11}$ are selected from hydrogen, halogen, alkoxy groups, amino, or amino substituted with one or two alkyl or aryl groups. A preferred group of compounds has one of $R^5$, $R^6$, $R^{12}$ or $R^{10}$ as a chlorine and the other of $R^4$ to $R^{11}$ are hydrogen atoms.

Pairs of adjacent groups, i.e. $R^4$ and $R^5$, or $R^5$ and $R^6$, or $R^6$ and $R^7$, or $R^8$ and $R^9$, or $R^9$ and $R^{10}$, or $R^{10}$ and $R^{11}$ can be joined together as a carbocyclic or heterocyclic ring system comprising at least one 5 or 6-membered ring which is fused to the ring bearing the exocyclic double bond. When an additional fused ring is present it is preferably an additional fused benzene ring making the resulting compound a benzacridan derivative.

Specific compounds within the scope of the invention include, without limitation:

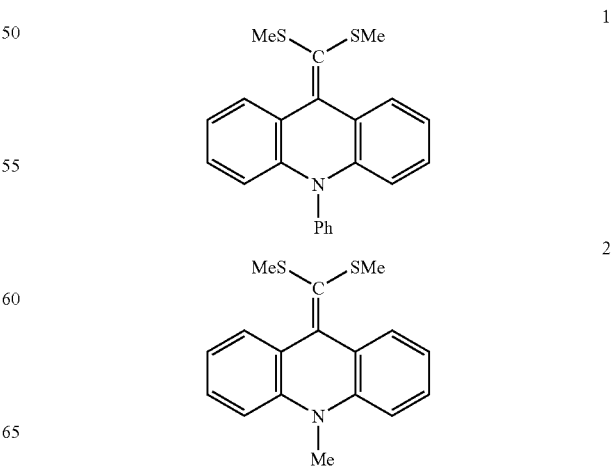

-continued

-continued

16

17

18

19

20

21

-continued

22

23

24

25

26

-continued
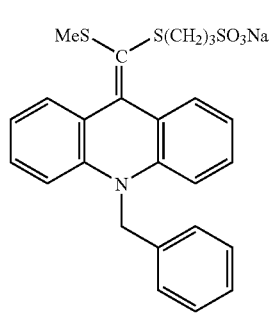
Lumigen PS-atto
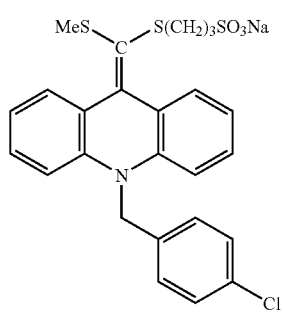
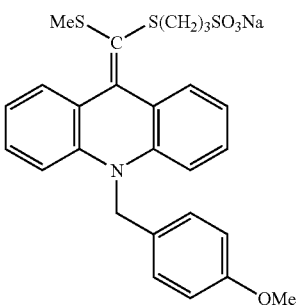
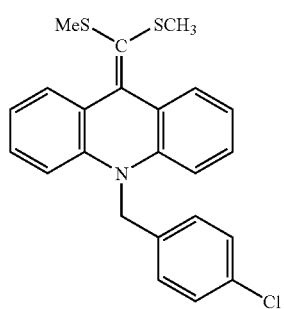
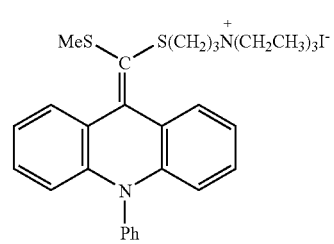
-continued
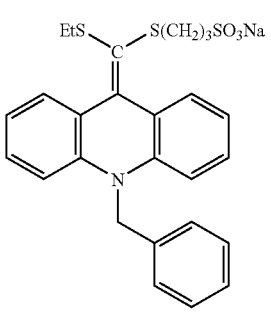
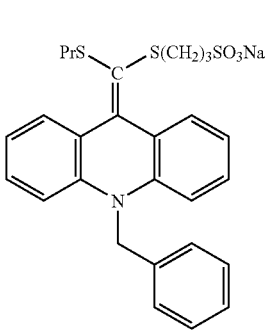
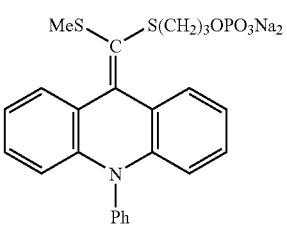
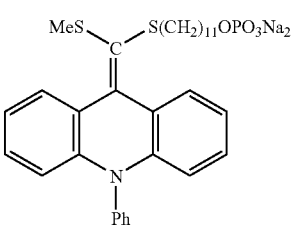
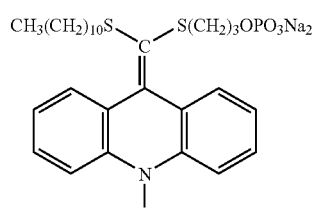
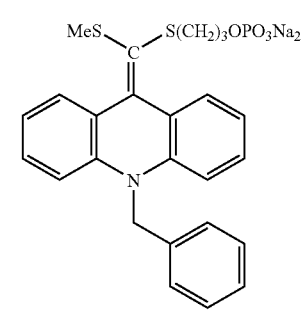

-continued
38
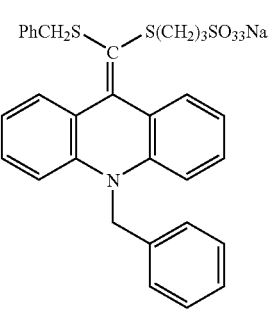
39
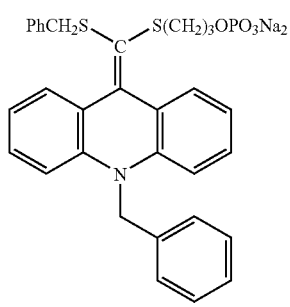
40
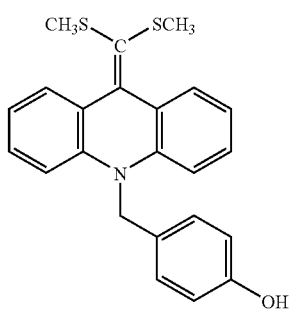
41
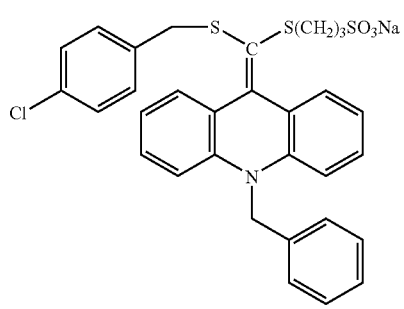
42
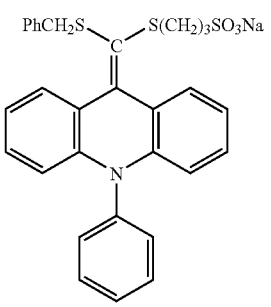
-continued
43
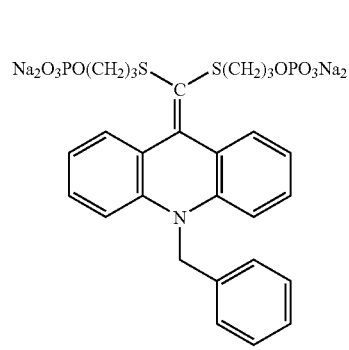
44
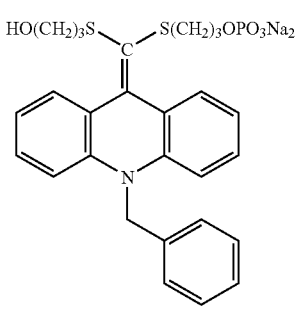
45
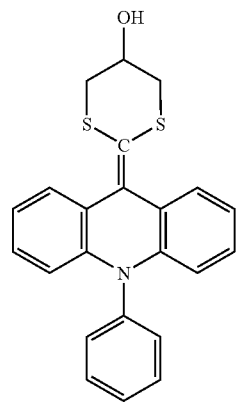
46
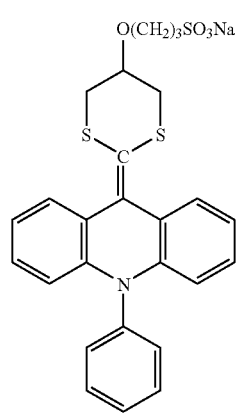
Lumigen TMA-6

-continued
47
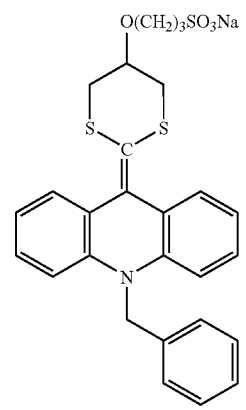
48
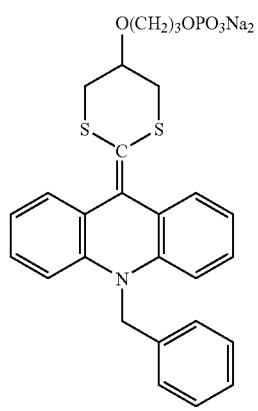
49
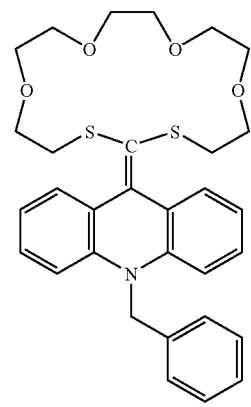
50
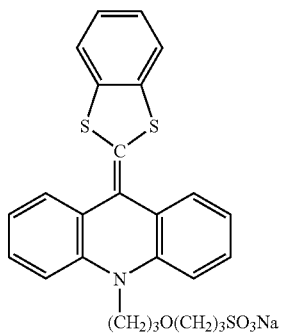
-continued
51
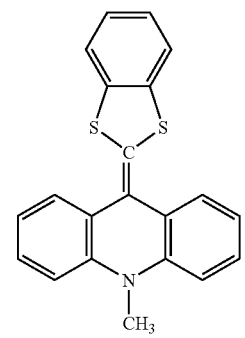
52
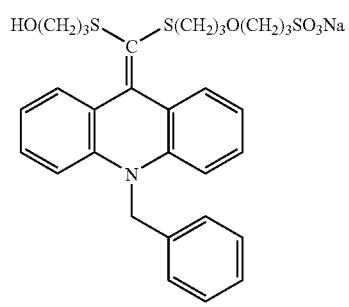
53
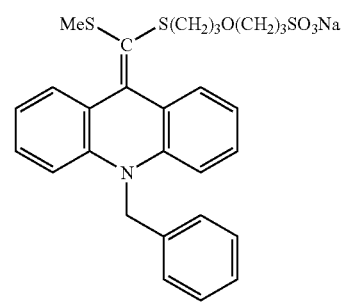
54
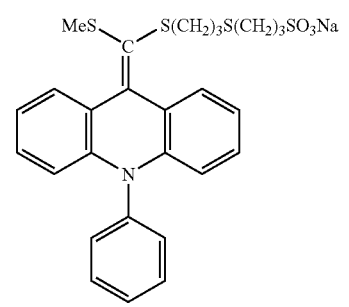
55
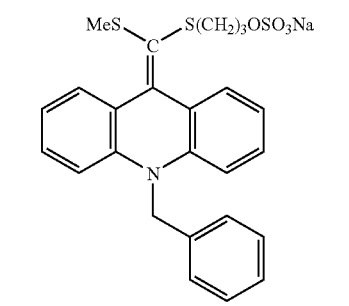

-continued

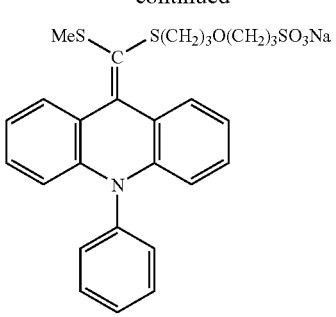

56

Preferred combinations of groups $R^1$-$R^3$ include compounds wherein one or both of $R^1$ and $R^2$ comprise an alkyl group substituted with a sulfonate salt group or a phosphate salt group and $R^3$ is phenyl, substituted phenyl, benzyl or substituted benzyl. When only one sulfonate or phosphate-substituted alkyl group is present, the other of $R^1$ or $R^2$ is preferably alkyl or benzyl.

Also considered within the scope of the present inventive class of compounds are embodiments in which $R^1$ or $R^2$ or both are joined to the nearest position, i.e. $R^4$ or $R^{11}$, of the acridan ring to close an additional ring.

In yet additional embodiments the nitrogen atom is joined to either of the nearest positions of the acridan ring $R^7$ or $R^8$ to close an additional 5-7 membered ring and $R^1$ and $R^2$ are independently selected from alkyl, substituted alkyl, aryl, substituted aryl, aralkyl and substituted aralkyl groups of 1-20 carbon atoms and can be joined together to form a ring of 5 to 30 atoms or $R^1$ or $R^2$ or both can be joined to the nearest position of the acridan ring to close an additional ring. Illustrative structures include:

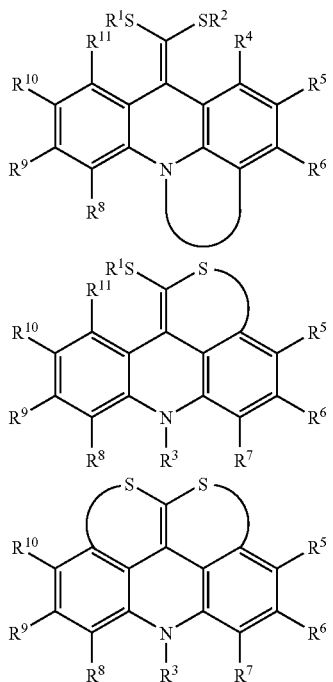

Reaction of ketene dithioacetal compounds of formula I, including those shown above, with peroxide and a peroxidase generate chemiluminescence which rapidly reaches very high intensity. Maximum light emission is achieved in one minute or less and remains constant for several minutes. No other known chemiluminescent peroxidase substrate generates high intensity chemiluminescence so rapidly. This kinetic behavior in unexpected and contrasts with the chemiluminescence time profile of structurally related compounds disclosed in the aforementioned U.S. Pat. No. 5,922,558. For example, a compound having the formula:

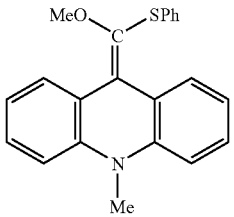

reacted with HRP was disclosed to reach maximum chemiluminescence intensity in 7 min. The ability of the compounds of the present invention to reach a stable maximum light intensity so rapidly makes them more suitable than other compounds for the rapid high throughput assays in demand today.

The present compounds exhibit unexpectedly high stability over the pH range of at least 5 to 10.5 allowing their formulation and use at both acid and alkaline pH values. Aqueous buffered solutions of compounds of formula I exhibit extended storage stability at room temperature and are indefinitely stable at 4° C. Solutions of compounds of formula I bearing water solubilizing groups can be prepared at their working concentrations and require no cosolvents. Enhanced reagent formulations have been prepared which permit sensitive detection at pH 5-6, the pH of optimum activity of horseradish peroxidase.

Methods of preparing compounds of formula I include nucleophilic addition of a lithiosilane compound or a phosphorus ylide to a suitable carbonyl compound according to the two schemes below (F. A. Carey, A. S. Court, J. Org. Chem., 37, 1926-29, (1972)).

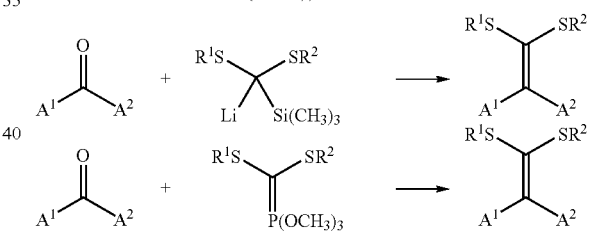

In another method, an ester is converted to a ketene-dithioacetal by reaction with a bis(dialkylaluminum)-dithiol reagent as disclosed in E. J. Corey and A. P. Kozikowski, Tetrahedron Lett., 925-8 (1975) and shown below.

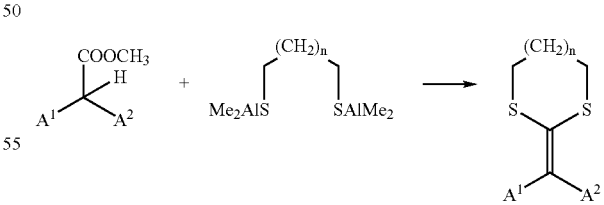

In yet another method, an anion of an active methylene group is reacted with $CS_2$ and the dithiocarboxylate is reacted with a reagent $R^1$-LG containing the $R^1$ group to form a dithioester. An example of the latter methodology is disclosed in I. Shahak and Y. Sasson, Tetrahedron Lett., 4207-10 (1973). The dithioester is converted to the enolate and reacted with a reagent of the formula $R^2$-LG. Typical leaving groups include halogens, such as chloride, bromide and iodide, sulfonates such as methanesulfonate and p-toluenesulfonate and trifluoromethanesulfonate, carboxylates such as acetate and benzoate particularly when X is an acyl group in which case X-LG would be an acid anhydride, sulfates such as methosulfate, and other groups such as imidazole, triazole and tetrazole, maleimide, succinimidoxy groups.

Method A

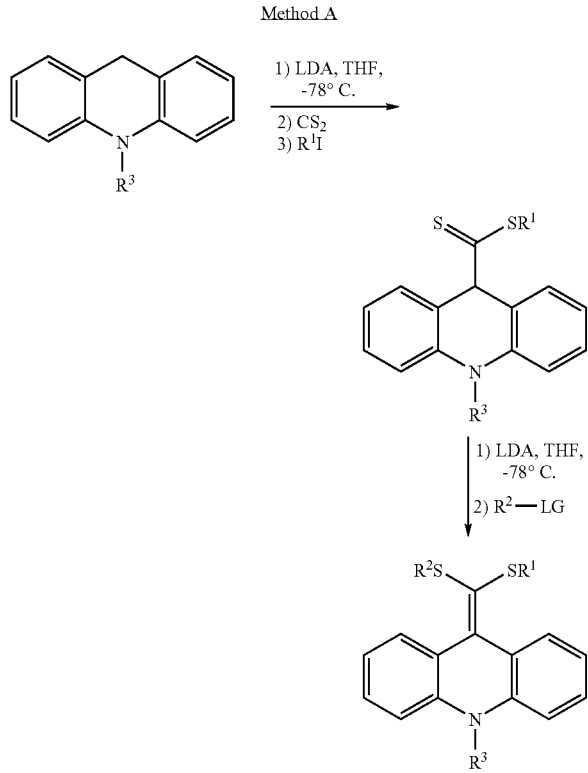

Method B

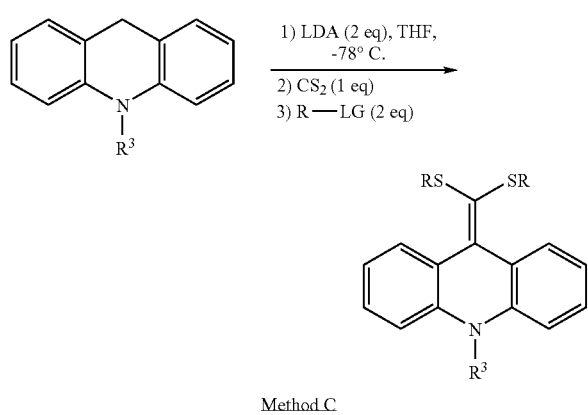

Method C

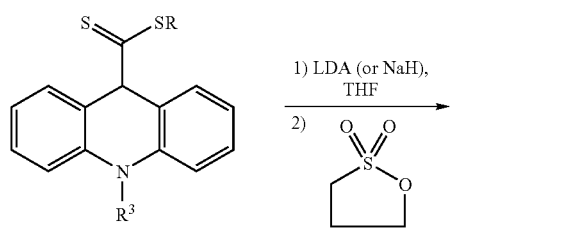

-continued

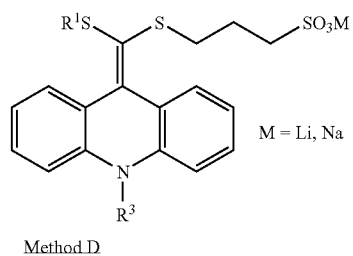

M = Li, Na

Method D

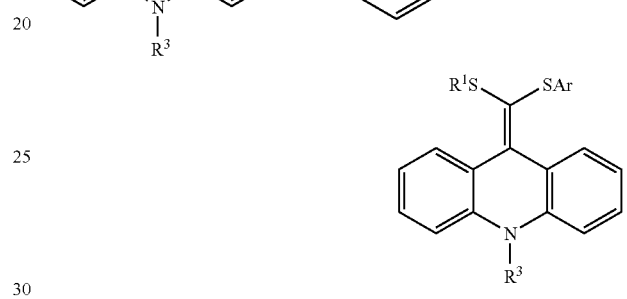

Method D above involves generation of a benzyne intermediate as the reactive arylating species. The benzyne intermediate can be generated in situ by for example treatment of a brominated benzene compound with a strong base such as sec-butyl lithium or LDA (M. Watanabe, et al., Chem. Pharm. Bull., 37(1), 36-41 (1989).

Another synthetic method comprises reaction of a phosphorus ylide derived from benzodithiole with an acridone compound. Procedures and conditions are described generally in the aforementioned Akiba, et al. reference as well as in K. Ishikawa, K. Akiba and N. Inamoto, Tetrahedron Lett., 41, 3695-3698 (1976).

Compounds and compositions of the present invention are useful in a method to produce chemiluminescence by reaction with a peroxidase. Reaction of a compound of the invention with a peroxidase and a peroxide in an aqueous buffer solution produces easily detectable visible chemiluminescence. Light intensity reaches a maximum level rapidly at room temperature, typically in about 1 minute. The reaction is conducted optionally in the presence of an enhancer.

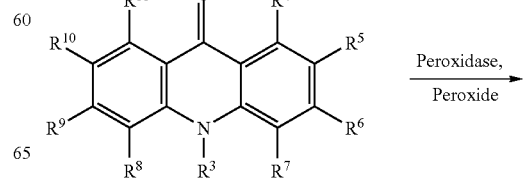

-continued

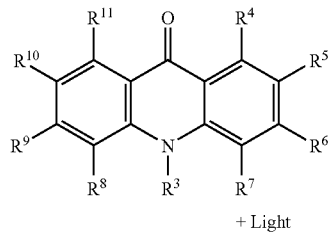

+ Light

In a preferred method of producing chemiluminescence, compound I is reacted with a peroxidase, a peroxide and an enhancer in an alkaline buffer with a pH between about 8 and 10 to produce a continuous chemiluminescence signal which commences upon reaction of the enzyme and the compound I. Analytical sensitivity can be increased by incorporation of a non-ionic surfactant as will be described in more detail below.

In a preferred method of producing light from the reaction of compound I with a peroxidase, the reaction is performed at a temperature between 5° C. and 50° C., preferably between 20° C. and 40° C. in an aqueous buffer solution at a pH between about 5 and 10.5, preferably between 7 and 10. Compound I is used at a concentration between 1 µM and 20 mM, preferably between 10 µM and 5 mM. The enzyme can be a free peroxidase or a peroxidase conjugate.

Compounds of the present invention typically produce light over a 100-200 nm wide band of emission, which exhibits a maximum intensity at wavelengths in the near ultraviolet to the visible region of the electromagnetic spectrum. Typical wavelengths of maximum intensity $\lambda_{max}$ in the range of 350-500 nm. It is contemplated that compounds of formula I bearing a covalently linked fluorophore could undergo intramolecular energy transfer resulting in emission at longer wavelengths from the excited state of the fluorophore.

More than one compound of formula I can be used concurrently in a method for producing light by the action of a peroxidase. It can be advantageous in some instances to simultaneously react two or more compounds of formula I with the peroxidase. When the two or more compounds have differing luminescent or physical properties, the combination of the two may be desirable to produce a light emitting reaction with characteristics not readily achievable through the use of any one compound. Examples of luminescent and physical properties which can differ between compounds I include emission spectrum, duration of light emission, enzyme turnover, rate of rise of emission to maximum, hydrophobicity/hydrophilicity and solubility.

The peroxide component is any peroxide or alkyl hydroperoxide capable of reacting with the peroxidase. Preferred peroxides include hydrogen peroxide, urea peroxide, and perborate salts.

The peroxidase which can undergo the chemiluminescent reaction include lactoperoxidase, microperoxidase, myeloperoxidase, haloperoxidase, e.g. vanadium bromoperoxidase, horseradish peroxidase, fungal peroxidases such as lignin peroxidase and peroxidase from Arthromyces ramosus and Mn-dependent peroxidase produced in white rot fungi, and soybean peroxidase. Other peroxidase mimetic compounds which are not enzymes but possess peroxidase-like activity including iron complexes and Mn-TPPS$_4$ (Y. -X. Ci, et al., Mikrochem. J., 52, 257-62 (1995)) are known which catalyze the chemiluminescent oxidation of luminol are explicitly considered to be within the scope of the meaning of peroxidase as used herein.

Conjugates or complexes of a peroxidase and a biological molecule can also be used in the method for producing chemiluminescence, the only proviso being that the conjugate display peroxidase activity. Biological molecules which can be conjugated to one or more molecules of a peroxidase include DNA, RNA, oligonucleotides, antibodies, antibody fragments, antibody-DNA chimeras, antigens, haptens, proteins, lectins, avidin, streptavidin and biotin. Complexes including or incorporating a peroxidase such as liposomes, micelles, vesicles and polymers which are functionalized for attachment to biological molecules can also be used in the methods of the present invention.

Incorporation of certain enhancer compounds into the reaction mixture promotes the reactivity of the enzyme. Included among these enhancers are phenolic compounds and aromatic amines known to enhance other peroxidase reactions as described in the aforementioned references by Thorpe & Kricka and by Ii, et al., and in U.S. Pat. Nos. 5,171,668 and 5,206,149 which are incorporated herein by reference. Substituted and unsubstituted arylboronic acid compounds and their ester and anhydride derivatives as disclosed in U.S. Pat. No. 5,512,451 and incorporated herein by reference are also considered to be within the scope of enhancers useful in the present invention. Preferred enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol. Mixtures of more than one enhancer from those classes mentioned above can also be employed.

Additional enhancers found to be effective in enhancing the production of chemiluminescence from compounds of the present invention are derivatives of phenoxazine and phenothiazine having the formulas below.

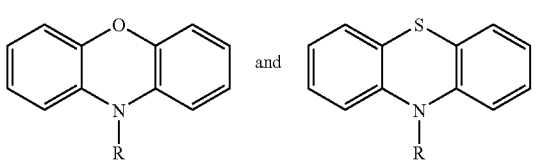

R groups substituted on the nitrogen atom of phenoxazine and phenothiazine enhancers include alkyl of 1-8 carbon atoms, and alkyl of 1-8 carbon atoms substituted with a sulfonate salt or carboxylate salt group. Preferred enhancers include 3-(N-phenothiazinyl)propanesulfonic acid salts, 3-(N-phenoxazinyl)propanesulfonic acid salts, 4-(N-phenoxazinyl)butanesulfonic acid salts, 5-(N-phenoxazinyl) pentanoic acid salts and N-methyl-phenoxazine and related homologs.

Nonionic surfactant additives in the present chemiluminescent reagents is useful for solubilizing purposes. Incorporation of nonionic surfactants into reactions for producing chemiluminescence by the use of a peroxidase may lead to an improvement in analytical sensitivity with respect to the peroxidase. Nonionic surfactants useful in the practice of the present invention include by way of example polyoxyethylenated alkylphenols, polyoxyethylenated alcohols, polyoxyethylenated ethers and polyoxyethylenated sorbitol esters.

Cationic surfactants, including quaternary ammonium salt compounds such as CTAB, are advantageous for use in increasing the level of chemiluminescence emitted when certain compounds of the present invention are reacted with a peroxidase and a peroxide. For example, light intensity from the reaction of compound 11 shown below according to the present invention was increased more than 20-fold when CTAB was included in the reaction mixture.

The reaction of the present invention is carried out in solution such as an aqueous buffer which may be in contact with the surface of a solid support such as a bead, tube, membrane or microwell plate coated with peroxidase. Suitable buffers include any of the commonly used buffers capable of maintaining a pH in the range of about 5 to about 10.5 for example, phosphate, borate, acetate, carbonate, tris(hydroxymethylamino)methane, glycine, tricine, 2-amino-2-methyl-1-propanol, diethanolamine and the like. The preferred method of practicing the invention in this regard is determined by the requirements of the particular intended use.

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

An important use of the present chemiluminescent methods is for detecting the presence or amount of an analyte in an assay procedure by a chemiluminescent reaction. The method comprises the steps of contacting a sample suspected of containing the analyte with a chemiluminescent compound of the present invention, a source of peroxide and a peroxidase, detecting the light produced in a qualitative method and, if quantitation is desired, relating the amount of light produced to the amount of the analyte. The relationship between light intensity and amount of analyte can be easily discerned by constructing a calibration curve with known amounts of the analyte. Compound I is typically used in a concentration of about $10^{-5}$ M to about $10^{-2}$ M, preferably between about $10^{-4}$ M and about $10^{-3}$ M. The peroxidase is preferably below about $10^{-9}$ M when detected in a solution. Typical samples which are analyzed by the chemiluminescent reaction method are body fluids such as blood, plasma, serum, urine, semen, saliva, CSF and the like.

Analytes which can be assayed by the present methods include peroxidases, in which case it would be unnecessary to add additional peroxidase, inhibitors of peroxidases, and various classes of organic and biological molecules which can be labeled with a peroxidase or can be specifically detected through enzyme-labeled specific binding partners. The enzyme can be incorporated directly as the label on the analyte binding compound. Alternately the analyte binding compound can be bound to at least one enzyme-labeled specific binding substance for the analyte binding compound. Alternately the analyte binding compound can be labeled with at least one second specific binding substance which is then bound to a enzyme-labeled binding partner for the second specific binding substance.

The present invention also relates to the use of this method for detecting hydrogen peroxide in an assay procedure by a chemiluminescent reaction with a compound of formula I and a peroxidase enzyme, wherein the amount of light produced is related to the presence or amount of the peroxide present. It will be apparent to those skilled in the art of chemiluminescent assays that the present methods can be used to detect oxidase enzymes and dehydrogenase enzymes. These enzymes generate hydrogen peroxide through reduction of oxygen and oxidation of their native substrates. The hydrogen peroxide thereby produced can then be further reacted either concurrently as it is generated or in a subsequent step with compound I of the present invention and a peroxidase to produce light. A property of the light produced is then related to the amount of the oxidase or dehydrogenase enzyme. Further the oxidase or dehydrogenase enzyme may be present as a conjugate to a biological molecule or a member of a specific binding pair in an assay for an analyte.

The reaction of a compound of formula I with a peroxidase to produce chemiluminescence constitutes a rapid and sensitive method for detecting the presence or amount of the peroxidase. Use of the present method can therefore be made for the purpose of determining the presence or quantity of a peroxidase in a sample by measuring the amount or intensity of light produced by reaction of the sample with a compound of formula I. Such a determination can find use e.g. in detecting the peroxidase activity of mammalian blood as evidence in forensic investigations.

A second area of application for the chemiluminescent measurement of peroxidase activity is in the detection and measurement of enzyme inhibitors. For example, peroxidase inhibitors include cyanide, sulfide and high concentrations of hydrogen peroxide. Measurement of the quantity or characteristics of an inhibitor, such as the inhibition constant $K_i$, or half-life for inhibition, $t_{1/2}$, is made by measuring the activity of a sample containing the peroxidase enzyme in the presence of a substrate of formula I producing a detectable product and a quantity of the inhibitor. Reaction of the enzyme and chemiluminescent compound is made in the presence and absence of the inhibitor and the results are compared to determine the presence or amount of the inhibitor. The effect of the inhibitor can have one or more of any of three effects, a decrease in light intensity, a slower rate of rise of light intensity or a delay period before light emission begins.

Since the reaction is catalyzed by the peroxidase, exceedingly small quantities of the enzyme are sufficient to produce a detectable amount of light. Sensitivities below 1 amol ($1 \times 10^{-18}$ mol) have been achieved. The ability to detect such small amounts of peroxidase make the present chemiluminescent technology suitable for analyses of many types of analytes using enzyme-linked assays which can detect small quantities of analyte present in low abundance in a sample or in a sample of limited size. In this type of assay, a peroxidase is conjugated to one member of a specific binding pair. An example is a chemiluminescent enzyme-linked immunoassays, such as an ELISA. Various assay formats and the protocols for performing the immunochemical steps are well known in the art and include both competitive assays and sandwich assays. The detectably labeled binding pair so formed can be assayed with the compounds and methods of the present invention. When the detectable label is the peroxidase enzyme, it is detected directly. When the detectable label is a member of another specific binding pair, e.g. a hapten, a conjugate of its binding partner with a peroxidase is reacted first and the peroxidase then detected in accordance with the present methods. Measurement can be performed with enzyme-labeled species attached to art-known solid surfaces or supports or free in solution or enclosed within an organized assembly such as a liposome in which case a lytic agent is employed to lyse the liposome and free the detectable enzyme.

Another exemplary use is the detection of proteins by the technique of western blotting. A sample containing a protein analyte is detected with a specific primary antibody and an enzyme-labeled secondary antibody which recognizes and binds to the primary antibody. The label enzyme is detected by chemiluminescence using a compound of the present invention as the chemiluminescent assay using a reagent of the invention. Variations on this technique such as using biotinylated antibodies and avidin-HRP are considered within the scope of assays able to be performed using the inventive methods.

Compounds of the present invention are also useful for the detection of nucleic acids by the use of enzyme-labeled nucleic acid probes. Exemplary methods include solution hybridization assays, DNA detection in Southern blotting, RNA by Northern blotting, DNA sequencing, DNA fingerprinting, colony hybridizations and plaque lifts, the conduct of which is well known to those of skill in the art. To adapt these methods for use with the present compounds a peroxidase enzyme is used as a label. The peroxidase can be present as a direct conjugate with a probe oligonucleotide or capture oligonucleotide or it can be incorporated through indirect linking means using art-known methods.

In addition to the aforementioned antigen-antibody, hapten-antibody or antibody-antibody pairs, specific binding pairs also can include complementary oligonucleotides or polynucleotides, avidin-biotin, strept-avidin-biotin, hormone-receptor, lectin-carbohydrate, IgG-protein A, nucleic acid-nucleic acid binding protein and nucleic acid-anti-nucleic acid antibody.

In another aspect, the present invention relates to a reagent composition for producing chemiluminescence by reaction with a peroxidase comprising an aqueous buffer with a pH between about 5 and about 10.5, a compound of formula I at a concentration of 0.01-10 mM and a peroxide at a concentration of 0.01-10 mM. Optionally the compositions may further comprise at least one enhancer in an amount effective to enhance the chemiluminescence, preferably between 0.001 and 10 mg/mL. The composition may also optionally comprise a surfactant at a concentration between 0.01 and 10 mg/mL.

A preferred reagent composition for producing chemiluminescence by reaction with a peroxidase comprises an aqueous buffer with a pH between about 7.5 and about 9, a compound of formula I at a concentration of 0.01-10 mM, a peroxide at a concentration of 0.01-10 mM, an enhancer at a concentration of 0.001 and 10 mg/mL and a surfactant in an amount effective to enhance the chemiluminescence, preferably between 0.001 and 10 mg/mL. The formulation can further comprise a chelating agent such as EDTA at a concentration of 0.01-10 mM.

In order to more fully describe various aspects of the present invention, the following examples are presented which do not limit the scope of the invention in any way.

EXAMPLES

1. Synthesis of Ketene Dithioacetals. The following compounds were prepared.

| Compd. | $R^{4-11}$ | $R^3$ | $R^1$ | $R^2$ |
|---|---|---|---|---|
| 1 | — | Ph | Me | Me |
| 2 | — | Me | Me | Me |
| 3 | — | Ph | benzyl | benzyl |
| 4 | — | Ph | $CHPh_2$ | $CHPh_2$ |
| 5 | — | Ph | —$(CH_2)_3$— | |
| 6 | — | Ph | Me | n-octyl |
| 7 | — | Ph | Me | Ph |
| 8 | — | Ph | Me | $CH_2COOEt$ |
| 9 | — | Ph | Me | isopropyl |
| 10 | — | Ph | Me | 2-hydroxybutyl |
| 11 | — | Ph | Me | $(CH_2)_3SO_3Li$ |
| 12 | — | Ph | $(CH_2)_3SO_3Li$ | $(CH_2)_3SO_3Li$ |
| 13 | — | Ph | n-octyl | $(CH_2)_3SO_3Li$ |
| 14 | — | Ph | Me | $(CH_2)_3SO_3Na$ |
| 15 | — | Me | Me | $(CH_2)_3SO_3Na$ |
| 16 | — | Ph | Me | $(CH_2)_3I$ |
| 17 | 6-OMe | Ph | Me | Me |
| 18 | 6-OMe | Ph | Me | $(CH_2)_3SO_3Na$ |
| 19 | 6-Cl | Ph | Me | Me |
| 20 | — | Ph | Me | $CH_2Ph$ |
| 21 | — | An | Me | Me |
| 22 | — | An | Me | $(CH_2)_3SO_3Na$ |
| 23 | — | Np | Me | Me |
| 24 | — | Np | Me | $(CH_2)_3SO_3Na$ |
| 25 | 6-OMe | Me | Me | Me |
| 26 | — | $CH_2Ph$ | Me | Me |
| 27 | — | $CH_2Ph$ | Me | $(CH_2)_3SO_3Na$ |
| 28 | — | $CH_2$-p-$C_6H_4Cl$ | Me | $(CH_2)_3SO_3Na$ |
| 29 | — | $CH_2$-p-$C_6H_4OMe$ | Me | $(CH_2)_3SO_3Na$ |
| 30 | — | $CH_2$-p-$C_6H_4Cl$ | Me | Me |
| 31 | — | Ph | Me | $(CH_2)_3N^+(Et)_3I^-$ |
| 32 | — | $CH_2Ph$ | Et | $(CH_2)_3SO_3Na$ |
| 33 | — | $CH_2Ph$ | Pr | $(CH_2)_3SO_3Na$ |
| 34 | — | Ph | Me | $(CH_2)_3OPO_3Na_2$ |
| 35 | — | Ph | Me | $(CH_2)_{11}OPO_3Na_2$ |
| 36 | — | Ph | $C_{11}H_{23}$ | $(CH_2)_3OPO_3Na_2$ |
| 37 | — | $CH_2Ph$ | Me | $(CH_2)_3OPO_3Na_2$ |
| 38 | — | $CH_2Ph$ | $CH_2Ph$ | $(CH_2)_3SO_3Na$ |
| 39 | — | $CH_2Ph$ | $CH_2Ph$ | $(CH_2)_3OPO_3Na_2$ |

Me=methyl, Et=ethyl, Pr=n-propyl, Ph=phenyl, Np=2-naphthyl, An=p-anisyl (4-MeOPh), $R^4$-$R^{11}$ are H unless otherwise indicated. Compounds 3, 4 and 6 were obtained as mixtures of double bond isomers. Each of these compounds generates chemiluminescence in the present invention.

2. Preparation of N-Arylacridan Precursors. The compounds N-phenylacridan, N-(4-methoxy)phenylacridan and N-(2-naphthyl)acridan were prepared by a palladium-catalyzed coupling of acridan and a halogenated aromatic compound, preferably an aryl iodide or aryl bromide. For example, bromobenzene, 4-bromoanisole and 2-bromonaphthalene can be used in the coupling reaction. The palladium-catalyzed step was performed using methods generally known in the literature using a palladium catalyst formed from a tertiary phosphine and a palladium compound such as PdCl$_2$ or Pd(OAc)$_2$.

3. Representative Synthetic Procedures.

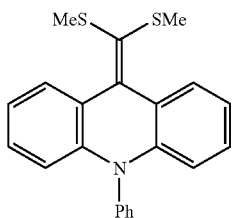

1

Synthesis of Compound 1. To an LDA solution (37 mmol) prepared from diisopropylamine and n-butyllithium in THF (150 mL) at −78° C. was added the N-phenylacridan (9.00 g, 35 mmol) in THF (50 mL). The mixture was stirred at −78° C. for 1 hr. CS$_2$ (2.35 mL, 39 mmol) was then added. After 1 hr at −78° C., the reaction was allowed to warm up slowly to room temperature (1 hr). The reaction mixture was cooled down to −78° C. again when MeI (2.86 mL, 46 mmol) was added. After the addition, the dry ice bath was removed and the reaction was continued at room temperature for 2 hrs. The reaction mixture was then evaporated in vacuo and the residue was subject to column chromatography (hexanes/CH$_2$Cl$_2$ 7:1), giving 9.21 g of methyl N-phenyl-acridan-9-dithiocarboxylate as a yellow crystalline solid.

Yield 76%. $^1$H NMR(CDCl$_3$): d 2.54 (s, 3H), 6.02 (s, 1H), 6.37 (d, 2H), 6.92 (t, 2H), 7.07 (t, 2H). 7.35-7.43 (m, 4H), 7.53 (m, 1H), 7.64 (m, 2H).

To an LDA solution (1.1 mmol) in THF (30 mL) at −78° C. was added the dithioester (0.347 g, 1 mmol) in THF (5 mL). The mixture was stirred at −78° C. for 1 hr. MeI (0.10 mL, 1.6 mmol) was then added via a syringe at −78° C. The resulting mixture was stirred overnight at room temperature. After removal of solvent in vacuum, the residue was chromatographed on silica gel (hexanes/EtOAc 20:1), giving 0.317 g of Compound 1 as a slightly yellowish solid (88% yield). $^1$H NMR (CDCl$_3$): d 2.37 (s, 6H), 6.52 (d, 2H), 7.07-7.18 (m, 4H), 7.41 (d, 2H), 7.57 (m, 1H), 7.67 (m, 2H), 7.97 (dd, 2H).

Compounds 2, 6, 8, 9, 10, 16, 17, 19, 20, 21, 23, 26, and 30 were also prepared by an analogous procedure from the corresponding dithioester intermediates using either LDA or NaH as the base.

Compound 2. Yield 80%. $^1$H NMR (CDCl$_3$): δ 2.29 (s, 6H), 3.48 (s, 3H), 7.01-7.09 (m, 4H), 7.30 (m, 2H), 7.82 (dd, 2H).

Compound 6. Yield 29%. $^1$H NMR (CDCl$_3$): δ 0.88 (t, 3H), 1.20 (br, 10H), 1.49 (m, 2H), 2.32 (s, 3H), 2.71 (t, 2H), 6.47 (t, 2H), 7.04-7.10 (m, 4H), 7.36 (d, 2H), 7.54 (m, 1H), 7.64 (m, 2H), 7.90 (dd, 1H), 7.96 (dd, 1H).

Compound 8. Yield 63%. $^1$H NMR (CDCl$_3$): δ 1.19 (t, 3H), 2.25 (s, 3H), 3.56 (s, 2H), 4.08 (q, 2H), 6.49 (d, 2H), 7.03-7.12 (m, 4H), 7.38 (d, 2H), 7.55 (m, 1H), 7.65 (m, 2H), 7.93 (dd, 1H), 8.00 (dd, 1H).

Compound 9. Yield 83%. $^1$H NMR (CDCl$_3$): δ 1.21 (d, 6H), 2.32 (s, 3H), 3.22 (m, 1H), 6.44-6.50 (m, 2H), 7.04-7.12 (m, 4H), 7.35 (d, 2H), 7.54 (m, 1H), 7.64 (m, 2H), 7.85 (dd, 1H), 8.03 (dd, 1H).

Compound 10. Yield 65%, using 1,2-epoxybutane as alkylating agent. $^1$H NMR (CDCl$_3$) δ 0.86 (t, 3H), 1.38 (p, 2H), 1.74 (br, 1H), 2.37 (s, 3H), 2.49 (dd, 1H), 3.02 (dd, 1H), 3.30 (m, 1H), 6.51 (dd, 2H), 7.03-7.16 (m, 4H), 7.35 (d, 2H), 7.55 (t, 1H), 7.62 (t, 2H), 7.92 (dd, 1H), 8.00 (dd, 1H).

Compound 16. Yield 96%. $^1$H NMR (CDCl$_3$): δ 2.35 (s, 6H), 6.51 (m, 2H), 7.08 (m, 4H), 7.43 (dd, 1H), 7.60 (m, 2H), 7.93 (m, 4H), 8.00 (d, 1H), 8.12 (d, 1H).

Compound 17. Yield 49%. $^1$H NMR (CDCl$_3$): δ 2.31 (s, 6H), 3.67 (s, 3H), 5.99 (d, 1H), 6.43 (dd, 1H), 6.63 (dd, 1H), 7.00-7.11 (m, 2H), 7.36 (d, 2H), 7.52 (m, 1H), 7.63 (m, 2H), 7.80 (d, 1H), 7.93 (dd, 1H).

Compound 19. Yield 90%. $^1$H NMR (CDCl$_3$): δ 2.29 (s, 3H), 2.40 (s, 3H), 6.37 (d, 1H), 6.48 (m, 1H), 6.97 (t, 1H), 7.01-7.17 (m, 3H), 7.36 (d, 2H), 7.54 (m, 1H), 7.64 (m, 2H), 7.73 (m, 1H).

Compound 20. Yield 86%. $^1$H NMR (CDCl$_3$): δ 2.20 (s, 3H), 3.94 (m, 2H), 6.52 (m, 2H), 7.00-7.16 (m, 4H), 7.25 (m, 5H), 7.37 (d, 2H), 7.58 (t, 1H), 7.68 (t, 2H), 7.80 (dd, 1H), 7.93 (dd, 1H).

Compound 21. Yield 96%. $^1$H NMR (CDCl 3): δ 2.30 (s, 6H), 3.92 (s, 3H), 6.50 (d, 2H), 7.00-7.15 (m, 6H), 7.28 (d, 2H), 7.87 (dd, 2H).

Compound 23. Yield 84%. $^1$H NMR (CDCl$_3$): δ 1.89 (p, 2H), 2.35 (s, 3H), 2.77 (t, 2H), 2.90 (t, 2H), 6.48 (t, 2H), 7.01-7.13 (m, 4H), 7.37 (d, 2H), 7.54 (m, 1H), 7.64 (m, 2H), 7.86 (d, 1H), 7.95 (d, 1H).

Compound 26. Yield 94%. $^1$H NMR (CDCl$_3$): δ 2.30 (s, 6H), 5.29 (s, 2H), 6.87 (d, 2H), 7.06 (t, 2H), 7.13-7.20 (m, 4H), 7.27-7.35 (m, 3H), 7.88 (d, 2H).

Compound 30. Yield 90%. $^1$H NMR (CDCl$_3$): δ 2.32 (s, 6H), 5.25 (s, 2H), 6.83 (d, 2H), 7.10 (m, 4H), 7.19 (d, 2H), 7.12 (d, 2H), 7.91 (d, 2H).

Alternate Procedure for Dithiocarboxylation. To a solution of N-benzylacridan (43.8 g) in THF (800 mL) under argon was added 67 mL of 2.5 M n-BuLi solution at −78° C. The mixture was stirred at −78° C. for 3 hours, the cooling bath was removed and stirring continued for another 30 min. The solution was again cooled to −78° C. and 10.65 mL of CS$_2$ was added. After 1 hr at −78° C., the reaction was allowed to warm up slowly to room temperature (1 hr). Methyl iodide (29.71 g) was added reaction was continued at room temperature over night. The reaction mixture was then evaporated in vacuo and the residue dissolved in CH$_2$Cl$_2$. Passage of the solution through a short plug of silica and evaporation of solvent left an orange solid which was crystallized from hot ethyl acetate (10 mL/g of solid).

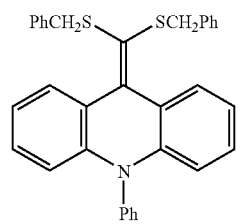

3

Synthesis of Compound 3. To an LDA solution (11.0 mmol) in THF (60 mL) at −78° C. was added N-phenylacridan (1.285 g, 5.0 mmol) in THF (20 mL). The resulting mixture was stirred at −78° C. for 1 h. CS$_2$ (0.33 mL, 5.5 mmol) was added. After 30 min. at −78° C., the reaction was slowly warmed to room temperature (1 h) and stirred for 30 min. The reaction was cooled to −78° C. when benzyl bromide (1.67 mL, 14 mmol) was added. After 20 min at −78° C., the reaction was allowed to warm and stirred at room temperature for 1.5 h. After workup, chromatography (hexanes/EtOAc 20:1) on silica gave 1.565 g of 3 (61% yield). $^1$H NMR (CDCl$_3$): δ 3.90 (s, 4H), 6.42 (d, 2H), 6.97 (t, 2H), 7.09 (t, 2H), 7.18-7.30 (m, 12H), 7.55 (m, 1H), 7.62-7.71 (dd, 4H) ppm.

Compounds 4 and 25 were prepared similarly.

Compound 4. Yield 26%. $^1$H NMR (CDCl$_3$): δ 5.95 (s, 4H), 6.38 (d, 2H), 6.88 (t, 2H), 7.07 (t, 2H), 7.12 (d, 2H), 7.21-7.30 (m, 20H), 7.40 (d, 2H), 7.53 (m, 1H), 7.61 (m, 2H).

Compound 25. Yield 16%. $^1$H NMR (CDCl$_3$): δ 2.28 (d, 6H), 3.44 (s, 3H), 3.86 (s, 3H), 6.54 (d, 1H), 6.63 (dd, 1H), 7.00-7.08 (m, 2H), 7.29 (m, 1H), 7.72 (d, 1H), 7.87 (d, 1H).

Similarly Compound 5 was prepared by alkylation of the corresponding dithiocarboxylate with 1,3-diiodopropane in THF in 44% yield. $^1$H NMR (CDCl$_3$): δ 2.16 (p, 2H), 2.90 (t, 4H), 6.44 (d, 2H), 6.99-7.10 (m, 4H), 7.38 (d, 2H), 7.54 (m, 1H), 7.64 (m, 2H), 7.71 (dd, 2H).

Compounds 11, 12, 14, 15, 18, 22, 24, 27, 28, 29, 32, 33 and 38 each containing one or two propanesulfonic acid salt groups were prepared by alkylating the dithiocarboxylate or dithiocarboxylate alkyl ester with propane sultone.

Compound 11 (yield 98%). $^1$H NMR (CD$_3$OD): δ 1.92 (p, 2H), 2.26 (s, 3H), 2.67 (t, 2H), 2.81 (t, 2H), 6.41 (t, 2H), 6.90-7.10 (m, 4H), 7.37 (d, 2H), 7.57 (t, 1H), 7.67 (t, 2H), 7.87 (d, 2H).

Compound 12 (yield 68%). $^1$H NMR (CD$_3$OD): δ 1.99 (p, 4H), 2.73 (t, 4H), 2.91 (t, 4H), 6.42 (d, 2H), 6.97-7.06 (m, 4H), 7.38 (d, 2H), 7.55 (t, 1H), 7.67 (t, 2H), 7.89 (dd, 2H).

Compound 14 (yield 53%). $^1$H NMR (CD$_3$OD): δ 1.88 (p, 2H), 2.22 (s, 3H), 2.63 (t, 2H), 2.78 (t, 2H), 6.37 (t, 2H), 6.90-7.05 (m, 4H), 7.32 (d, 2H), 7.52 (t, 1H), 7.63 (t, 2H), 7.83 (d, 2H).

Compound 15 Yield 94%. $^1$H NMR (CD$_3$OD): δ 1.87 (p, 2H), 2.21 (s, 3H), 2.64 (t, 2H), 2.81 (t, 2H), 3.45 (s, 3H), 6.90-7.09 (m, 4H), 7.24 (m, 2H), 7.79 (m, 2H).

Compound 18 Yield 84%. $^1$H NMR (CD$_3$OD): δ 1.93 (m, 2H), 2.26 (s, 3H), 2.69 (m, 2H), 2.82 (m, 2H), 3.61 (S, 3H), 5.91 (dd, 1H), 6.39 (t, 1H), 6.62 (m, 1H), 6.90-7.08 (m, 2H), 7.37 (d, 2H), 7.57 (t, 1H), 7.68 (t, 2H), 7.79 (dd, 1H), 7.90 (dd, 1H).

Compound 22 Yield 90%. $^1$H NMR (CD$_3$OD): δ 1.91 (p, 2H), 2.26 (s, 3H), 2.67 (t, 2H), 2.80 (t, 2H), 3.90 (s, 3H), 6.46 (t, 2H), 6.99 (m, 2H), 6.07 (m, 2H), 7.18-7.29 (m, 4H), 7.86 (d, 2H).

Compound 24 Yield 78%. $^1$H NMR (CD$_3$OD): δ 1.95 (p, 2H), 2.29 (s, 3H), 2.70 (t, 2H), 2.83 (t, 2H), 6.44 (dd, 2H), 7.03 (m, 4H), 7.40 (dd, 2H), 7.59 (m, 2H), 7.90 (d, 2H), 8.01 (m, 3H), 8.16 (d, 1H).

Compound 27 Yield 83%. $^1$H NMR (CD$_3$OD): δ 1.85 (p, 2H), 2.22 (s, 3H), 2.59 (t, 2H), 2.80 (t, 2H), 5.32 (s, 2H), 6.88 (d, 2H), 6.98 (m, 2H), 7.10 (m, 2H), 7.20-7.27 (m, 3H), 7.83 (dd, 2H).

Compound 28. Yield 87%. $^1$H NMR (CD$_3$OD): δ 1.85 (p, 2H), 2.22 (s, 3H), 2.60 (t, 2H), 2.80 (t, 2H), 5.30 (s, 2H), 6.86 (d, 2H), 6.96-7.17 (m, 6H), 7.27 (d, 2H), 7.80-7.87 (dd, 2H).

Compound 29. Yield 91%. $^1$H NMR (CD$_3$OD): δ 1.85 (p, 2H), 2.22 (s, 3H), 2.61 (t, 2H), 2.80 (t, 2H), 3.74 (s, 3H), 5.25 (s, 2H), 6.82 (d, 2H), 6.89-7.02 (m, 6H), 7.13 (t, 2H), 7.80-7.87 (dd, 2H).

Compound 32. $^1$H NMR (CD$_3$OD): δ 1.14 (t, 3H), 1.89 (p, 2H), 2.63 (t, 2H), 2.72 (q, 2H), 2.83 (t, 2H), 5.32 (s, 2H), 6.90 (m, 2H), 6.99 (m, 2H), 7.09-7.26 (m, 7H), 7.83 (d, 1H), 7.89 (d, 1H).

Compound 33. $^1$H NMR (CD$_3$OD): δ 0.82 (t, 3H), 1.46 (m, 2H), 1.92 (p, 2H), 2.68 (m, 4H), 2.83 (t, 2H), 5.32 (s, 2H), 6.91 (m, 2H), 6.97 (m, 2H), 7.1-7.25 (m, 7H), 7.86 (t, 2H).

Compound 38. $^1$H NMR (CD$_3$OD): δ 1.9 (p, 2H), 2.6 (t, 2H), 2.8 (t, 2H), 3.93 (s, 2H), 5.31 (s, 2H), 6.9 (m, 3H), 7.2 (m, 13H), 7.6 (d, 1H), 7.8 (d, 1H).

Synthesis of Compound 7. To a solution of LDA (2.5 mmol) in THF (30 mL) was added methyl N-phenylacridan-9-dithiocarboxylate (0.347 g, 1.0 mmol) in THF (10 mL). After 1 h at −78° C., the reaction was allowed to warm up to −20° C. and bromobenzene was then added. The reaction was allowed to slowly warm up after the addition and stirred at room temperature for 3 h. Removal of solvent in vacuo followed by chromatography (hexanes/EtOAc 20:1) afforded 0.255 g of Compound 7 (60% yield). $^1$H NMR (CDCl$_3$) δ 2.20 (s, 3H), 6.45 (d, 1H), 6.53 (d, 1H), 6.92 (t, 1H), 7.03-7.24 (m, 4H), 7.33-7.47 (m, 6H), 7.56 (m, 1H), 7.66 (m, 2H), 7.87-7.94 (m, 2H).

Synthesis of Compound 13. N-phenylacridan-9-dithiocarboxylate was converted to the n-octyl thioester by reaction with 1-iodooctane. To an LDA (4.48 mmol) solution in THF (70 mL) at −78° C. was added n-octyl N-phenylacridan -9-dithiocarboxylate (1.90 g, 4.26 mmol) in THF (20 mL). The resulting mixture was stirred at −78° C. for 1 h. 1,3-Propanesultone (0.78 g, 6.39 mmol) was then added in THF (10 mL). After 45 min. at −78° C., the reaction was allowed to warm up to room temperature and stirred further for 3 h. Removal of solvent gave a solid residue which was dissolved in a minimum volume of CH$_2$Cl$_2$ and precipitated with hexanes. The procedure was repeated until the solution showed no fluorescent component on a TLC plate. After drying in vacuum, 2.270 g of 13 was obtained as a yellowish powder. Yield 93%. $^1$H NMR (CDCl$_3$): δ 0.84 (t, 3H), 1.13-1.40 (m, 12H), 2.02 (q, 2H), 2.68 (t, 2H), 2.77 (t, 2H), 2.90 (t, 2H), 6.42 (dd, 2H), 6.94-7.08 (m, 4H), 7.34 (d, 2H), 7.56 (m, 1H), 7.67 (m, 2H), 7.86 (d, 1H), 7.92-(d, 1H).

Synthesis of Compound 31. Compound 16 (0.250 g, 0.49 mmol) in CH$_2$Cl$_2$ (5 mL) was stirred with triethylamine (9 mL) at room temperature for 2.5 days. The volatiles were removed in vacuum. The residue was dissolved in a minimum amount of CH$_2$Cl$_2$ and precipitated with ether. This procedure was repeated until the washes showed no fluorescent component. After drying in vacuum, 0.140 g of Compound 31 was obtained as a yellowish solid. Yield, 47%. $^1$H NMR (CD$_3$OD): δ 1.06 (m, 9H), 1.71 (m, 2H), 2.32 (s, 3H), 2.91-3.08 (m, 10H), 6.37 (d, 1H), 6.51 (d, 1H), 6.98-7.18 (m, 4H), 7.25 (d, 2H), 7.59 (m, 1H), 7.67 (m, 2H), 7.82 (d, 1H), 8.02 (d, 1H).

Synthesis of Compound 35. To a solution of methyl N-phenylacridan-9-dithiocarboxylate (1.735 g, 5.00 mmol) in THF (80 mL) was added NaH (0.460 g, 60% suspension in mineral oil, 11.5 mmol). The resulting mixture was stirred at room temperature for 3 h. 11-Bromoundecan-1-ol (1.633 g, 6.50 mmol) was then added in THF (20 mL). After overnight stirring, 4 mL of MeOH was added to the reaction mixture to decompose excess NaH. Removal of the solvent in vacuo gave a residue which was chromatographed on silica gel (hexane/EtOAc 4:1), giving the 11-hydroxyundecyl ketene dithioacetal derivative as a syrup, 2.550 g, yield 98%. 1H NMR (CDCl$_3$): δ 1.19-1.60 (m, 19H), 2.32 (s, 3H), 2.70 (t, 2H), 3.64 (m, 2H), 6.46 (t, 2H), 7.05 (m, 4H), 7.35 (d, 2H), 7.54 (m, 1H), 7.64 (m, 2H), 7.88 (dd, 1H), 7.95 (dd, 1H) ppm.

To a solution of the compound prepared above (2.55 g, 4.92 mmol) in CH$_2$Cl$_2$ (60 mL) at 0° C. was added pyridine (0.52 mL, 6.40 mmol) followed by POCl$_3$ (0.60 mL, 6.40 nmol). The reaction was continued at 0° C. for 1 h before the ice-bath was removed to allow the reaction to warm up to room temperature (30 min). 3-Hydroxypropionitrile (1.35 mL, 19.7 mmol) was then added in pyridine (3.18 mL, 39.4 mmol). After stirring overnight, the reaction mixture was washed with water in a separatory funnel. The organic phase, was dried over Na$_2$SO$_4$, evaporated and the residue chromatographed on silica gel (EtOAc) to give the bis(cyanoethyl)phosphate derivative, 2.70 g, yield 79%. $^1$H NMR (CDCl$_3$): δ 1.19-1.50 (m, 16H), 1.71 (m, 2H), 2.31 (s, 3H), 2.70 (t, 2H), 2.79 (t, 4H), 4.13 (q, 2H), 4.38 (q, 4H), 6.45 (t, 2H), 7.05 (m, 4H), 7.35 (d, 2H), 7.54 (m, 1H), 7.64 (m, 2H), 7.88 (dd, 1H), 7.94 (dd, 1H) ppm.

Hydrolysis of the cyanoethyl protecting groups was effected by was treatment of 2.70 g (3.84 mmol) of the protected phosphate with 1 M NaOH (7.68 mL, 7.68 mmol) in acetone (40 mL) overnight, giving 2.36 g of compound 35 (96% yield). $^1$H NMR (CD$_3$OD) δ 1.08-1.34 (m, 16H), 1.56 (m, 2H), 2.25 (s, 3H), 2.64 (t, 2H), 3.79 (q, 2H), 6.42 (d, 2H), 6.95-7.09 (m, 4H), 7.31 (d, 2H), 7.58 (m, 1H), 7.69 (m, 2H), 7.84 (d, 1H), 7.89 (d, 1H).

Compounds 34, 36 and 37 were prepared in a similar manner, 36 starting from the undecyl dithioester.

Compound 34 $^1$ NMR (CD$_3$OD): δ 1.77 (p, 2H), 2.24 (s, 3H), 2.85 (t, 2H), 3.79 (q, 2H), 6.39 (t, 2H), 6.94-7.07 (m, 4H), 7.32 (d, 2H), 7.56 (m, 1H), 7.67 (m, 2H), 7.83 (dd, 1H), 7.89 (dd, 1H).

Compound 36 $^1$H NMR (CD$_3$OD): δ 0.88 (t, 3H), 1.09-1.35 (m, 18H), 1.87 (p, 2H), 2.66 (t, 2H), 2.90 (t, 2H), 3.84 (q, 2H), 6.40 (m, 2H), 6.94-7.08 (m, 4H), 7.31 (d, 2H), 7.56 (m, 1H), 7.67 (m, 2H), 7.82 (d, 1H), 7.95 (d, 1H)

Compound 37 $^1$ NMR (CD$_3$OD) δ 1.75 (m, 2H), 2.24 (s, 3H), 2.89 (t, 2H), 3.83 (q, 2H), 5.35 (s, 2H), 6.92 (d, 2H), 7.01 (t, 2H), 7.15 (m, 4H), 7.29 (m, 3H), 7.88 (m, 2H).

4. Synthesis of Compound 39.

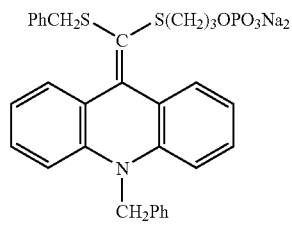

39

Compound 39 is prepared by the following synthetic process. Reaction of the anion of N-benzylacridan with CS$_2$ in THF at −78° C., allowing the reaction to warm up slowly to room temperature (1 hr) followed by addition of benzyl bromide yields the benzyl dithioester of N-benzylacridan. A solution of this dithioester in THF is treated with NaH and the resulting mixture stirred at room temperature. 3-Bromopropan-1-ol (1.633 g, 6.50 mmol) is then added and the reaction conducted overnight. The ketene dithioacetal thus formed is phosphorylated according to the process described in conection with the synthesis of compound 35.

5. Enhancement of Chemiluminescence from Ketene Dithioacetal Compounds. Several enhancers were tested in a test protocol involving reacting horseradish peroxidase with a solution of the enhancer, peroxide, EDTA and either compound 1 or 14 in a buffer containing Tween 20. Peak light intensity was determined. Among the preferred enhancers were 2-naphthol, 6-bromo-2-naphthol, p-hydroxy-cinnamic acid, 1,6-dibromo-2-naphthol, 7-methoxy-2-naphthol, 4-phenylphenol, 3-(N-phenothiazinyl)propanesulfonic acid salts, 3-(N-phenoxazinyl)propanesulfonic acid salts, 4-(N-phenoxazinyl)butanesulfonic acid salts, 5-(N-phenoxazinyl)pentanoic acid salts and N-methyl-phenoxazine.

6. Chemiluminescent Detection of HRP with Compound 1. Reagent compositions comprising 0.01 M tris buffer, pH 7.0, 0.5 mM urea peroxide, 0.1 mM p-phenylphenol, 1 mM EDTA, 0.025% Tween 20 and 5×10$^{-5}$ M compound 1 were tested for production of chemiluminescence by reacting triplicate 100 μL aliquots with 10 μL of HRP in the range 1.4×10$^{-15}$ to 1.4×10$^{-20}$ moles. Light production ensued upon mixing and reached maximum intensity in about 1 min. A log-log plot of chemiluminescence intensity vs. amount of enzyme was linear over the entire range tested.

7. Chemiluminescent Detection of HRP with Compound 14. Reagent compositions comprising 0.025 M tris buffer, pH 8.0, 2.5 mM urea peroxide, 4 mM p-hydroxycinnamic acid, 0.5 mM EDTA, 0.1% Tween 20 and 3×10$^{-4}$ M compound 14 were tested for production of chemiluminescence by reacting triplicate 100 μL aliquots with 10 μL of HRP in the range 1.4×10$^{-16}$ to 1.4×10$^{-20}$ moles. Light production ensued upon mixing and reached maximum intensity in about 1 min. The relation between chemiluminescence intensity and amount of enzyme is depicted in FIG. 1. For comparison, the relationship between S-B and amount of HRP is also shown for reference compound 1 having the formula:

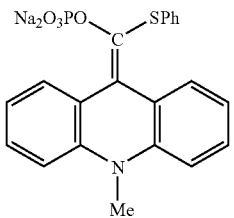

Ref. 1

The results for the reference compound were measured 15 minutes after addition of 10 μL of solutions of HRP containing between 1.4×10$^{-15}$ and 1.4×10$^{-19}$ moles of enzyme to 100 μL of the reagent comprising 0.055 M tris buffer, pH 8.6, 0.25 mM urea peroxide, 0.05 mM p-phenylphenol, 0.5 mM EDTA, 0.0125% Tween 20 and 3.3×10$^{-4}$ M of Ref 1.

Figure 2:
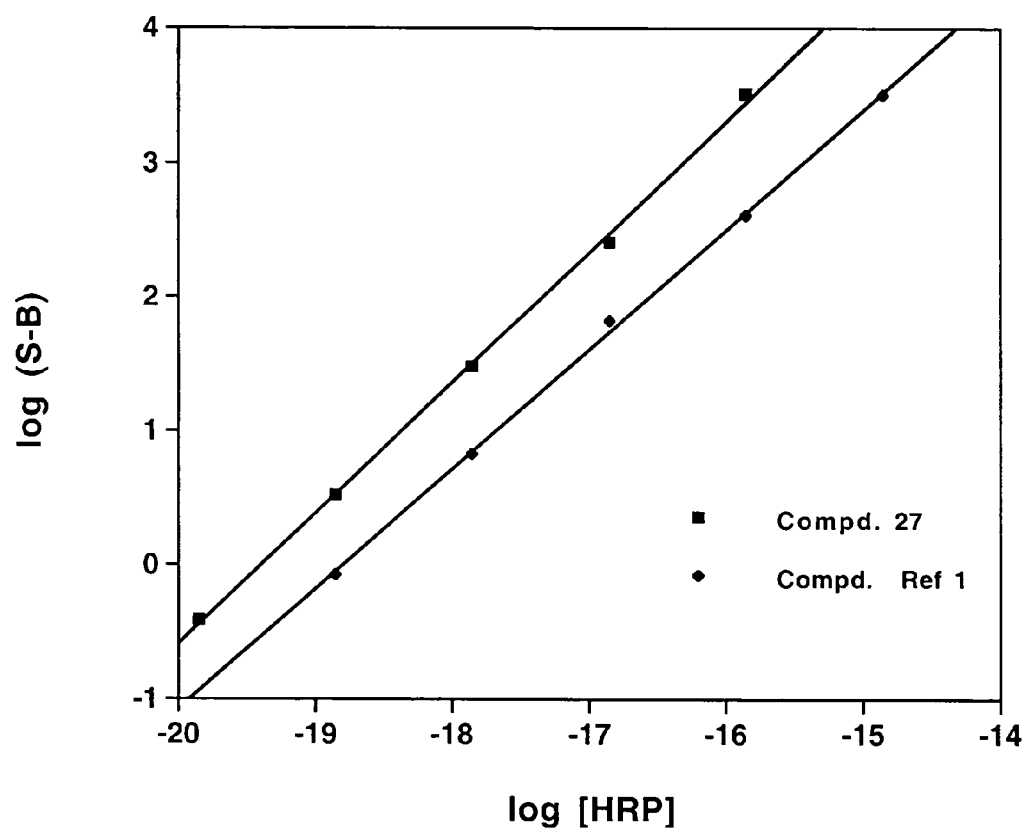
FIG. 2 is a graph relating the amount of HRP to the chemiluminescence intensity at 1.5 min emitted by 100 μL of a reagent described in Example 8 containing compound 27 triggered at room temperature. For comparison, the relationship between S-B and amount of HRP is also shown for reference compound 1 measured at 15 min.

8. Chemiluminescent Detection of HRP with Compound 27. Reagent compositions comprising 0.025 M tris buffer, pH 8.0, 2.5 mM urea peroxide, 4 mM p-hydroxycinnamic acid, 0.5 mM EDTA, 0.1% Tween 20 and $3\times10^{-4}$ M compound 27 were tested for production of chemiluminescence by reacting triplicate 100 µL aliquots with 10 µL of HRP in the range $1.4\times10^{-16}$ to $1.4\times10^{-20}$ moles. Light production ensued upon mixing and reached maximum intensity in about 1 min. The relation between chemiluminescence intensity at 1.5 min and amount of enzyme is depicted in FIG. 2 along with the results for Ref. compound 1 at 15 min as described above.

9. Comparison of Signal Intensity. Reagent compositions comprising 0.01 M tris buffer, pH 8, 0.5 mM urea peroxide, 0.1 mM p-phenylphenol, 1 mM EDTA, 0.025% Tween 20, and $5\times10^{-5}$ M of each compound in the table below except the compound designated Ref. 1 were tested for production of chemiluminescence by reacting a 100 µL aliquot with $3.5\times10^{-16}$ moles of HRP. The reagent formulation for Ref. 1 comprised 0.05 M tris buffer, pH 8.6, 0.25 mM urea peroxide, 0.05 mM p-phenylphenol, 0.5 mM EDTA, 0.0125% Tween 20, and $3.3\times10^{-4}$ M Ref. 1. For comparison, data are provided for reference compounds 1 and 2.

| Compound | Signal/Background |
|---|---|
| Ref. 1 | 53 |
| Ref. 2 | 325 |
| 1 | 8060 |
| 2 | 953 |
| 11 | 849 |
| 13 | 7626 |
| 14 | 688 |
| 26 | 5200 |
| 27 | 533 |

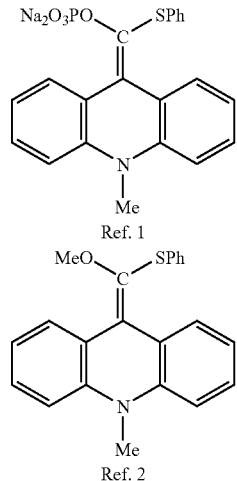

Ref. 1

Ref. 2

10. Comparison of Signal Intensity. The maximum signal produced by each of compounds 14, and 27-29 was compared by reacting a 100 µL aliquot of reagent compositions comprising 0.025 M tris buffer, pH 8, 2.5 mM urea peroxide, 4 mM p-hydroxycinnamic acid, 0.5 mM EDTA, 0.1% Tween 20, and $3\times10^{-4}$ M of the test compound with $3.5\times10^{-16}$ moles of HRP. Each reagent reached maximum light intensity in about 1 minute.

| Compound | Signal/Background |
|---|---|
| 14 | 2491 |
| 27 | 6933 |
| 28 | 6717 |
| 29 | 6621 |
| 38 | 26000 |

Figure 3:
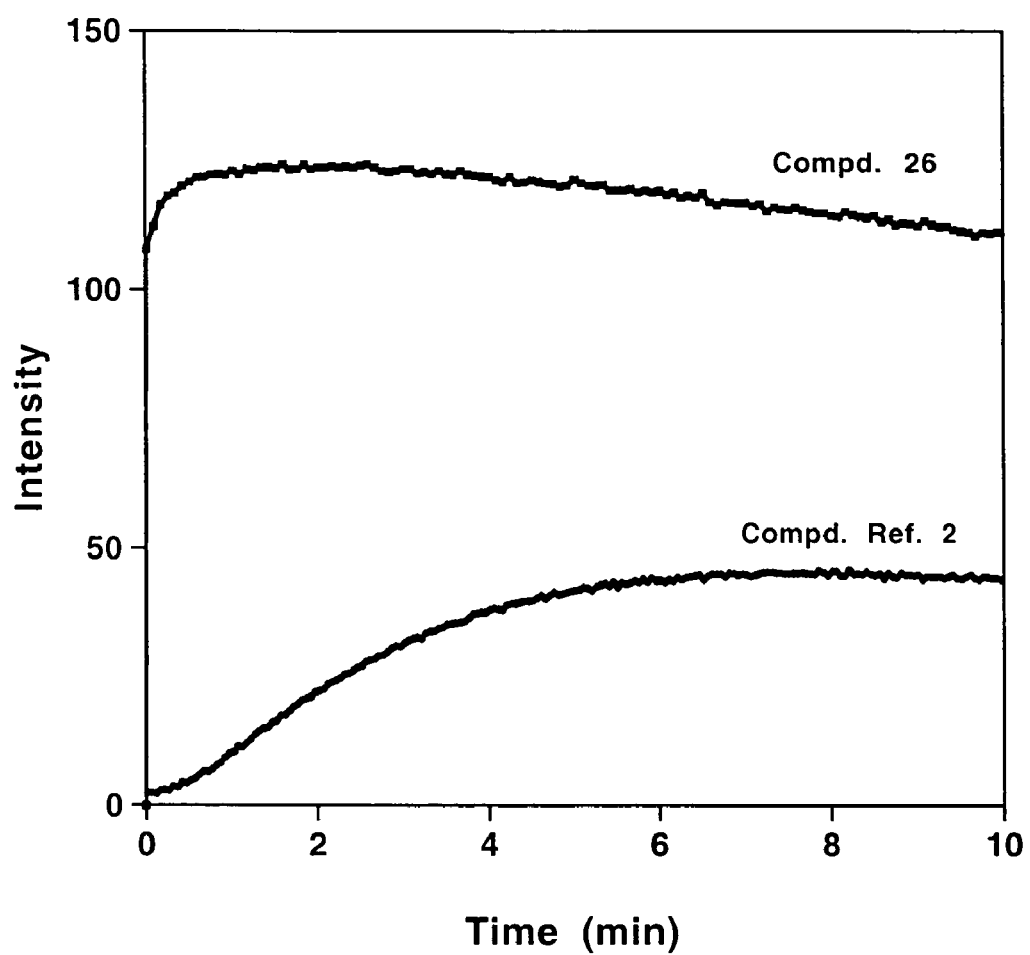
FIG. 3 is a graph showing the time profile of chemiluminescence resulting from reaction of $3.5\times10^{-16}$ moles of HRP at 25° C. with 100 μL of the reagent containing Compound 26 described in Example 11. The relative chemiluminescence time profile demonstrates the more rapid generation of chemiluminescence than a structurally similar compound designated Ref 2.

11. Chemiluminescence Time Profile using Ketene Dithioacetal 26. Reagent compositions comprising 0.01 M tris buffer, pH 8.0, 0.5 mM urea peroxide, 0.01 mM p-phenylphenol, 1 mM EDTA, 0.025% Tween 20, and $5\times10^{-5}$ M compound 26 were tested for production of chemiluminescence by reacting a 100 µL aliquot with $3.5\times10^{-16}$ moles of HRP. The relative chemiluminescence time profile is depicted in FIG. 3 and demonstrates the more rapid generation of chemiluminescence than the structurally similar compound designated Ref 2. The chemiluminescence time profile using the other ketene dithioacetals listed in Example 1 exhibited a similar rapid rise.

Figure 4:
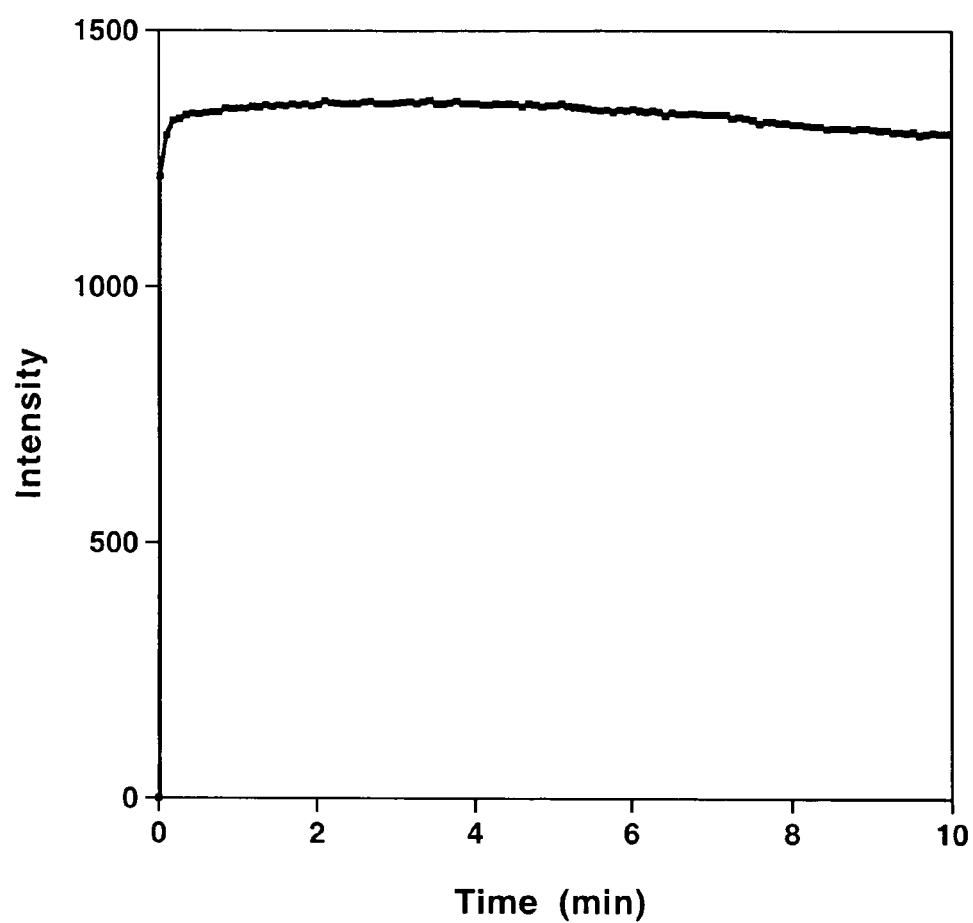
FIG. 4 is a graph showing the time profile of chemiluminescence resulting from reaction of $3.5\times10^{-16}$ moles of HRP at 25° C. with 100 μL of the reagent containing Compound 27 described in Example 12.

12. Chemiluminescence Time Profile using Ketene Dithioacetal 27. Reagent compositions comprising 0.025 M tris buffer, pH 8.0, 2.5 mM urea peroxide, 4 mM p-hydroxycinnamic acid, 0.5 mM EDTA, 0.1% Tween 20, and $3\times10^{-4}$ M compound 27 were tested for production of chemiluminescence by reacting a 100 µL aliquot with $3.5\times10^{-16}$ moles of HRP. The relative chemiluminescence time profile is depicted in FIG. 4 demonstrates the rapid generation of chemiluminescence and higher signal level generated than the reagents of the previous example.

Figure 5:
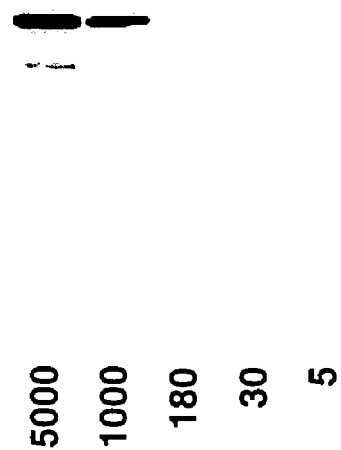
FIG. 5 is an image of x-ray films from a western blot assay of β-galactosidase via an HRP-labeled antibody on a PVDF membrane with chemiluminescent reagent compositions. Dilutions of β-galactosidase containing 5000, 1000, 180, 30 and 5 pg, respectively, of protein were detected with either a reagent of the invention containing compound 1 or, for comparison, with a reagent containing compound Ref. 1 as described in U.S. Pat. No. 5,922,558. Membranes were exposed to X-ray film for 5 s after a 11 min incubation in the respective detection reagents.
Figure 5:
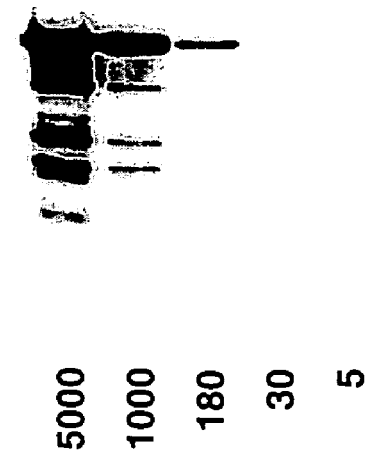

13. Western Blot using a Ketene Dithioacetal Substrate. A western blot assay of β-galactosidase as the test antigen was conducted according to the procedure described in U. K. Laermli, *Nature (London)*, 227, 680 (1970) using a PVDF membrane. β-Galactosidase standards in the range of 5000-5 pg. The detection reagent containing Compound 1 permitted detection to be performed in under 1 minute. FIG. 5 demonstrates the detection of β-gal after 11 min with a 5 second exposure. For comparison, the results of a western blot using a reagent containing compound Ref. 1 as described in U.S. Pat. No. 5,922,558 produced lower intensity chemiluminescence and required longer exposures to achieve the same image of the more abundant bands. In addition, the reagent of the invention was able to image lower abundance bands of 1 pg or less which were not possible to image with the reagent containing the reference compound.

Figure 6:
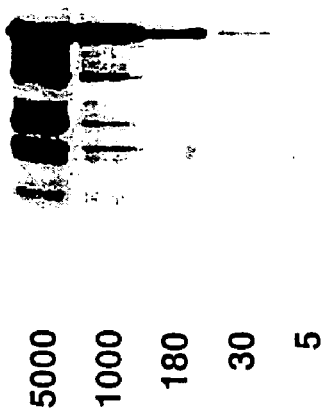
FIG. 6 depicts images of x-ray films from western blot assays of β-galactosidase via an HRP-labeled antibody on a PVDF membrane with chemiluminescent reagent compositions. Dilutions of β-galactosidase containing 5000, 1000, 180, 30 and 5 pg, respectively, of protein were detected with either a reagent of the invention containing compound 27 or compound 37.
Figure 6:
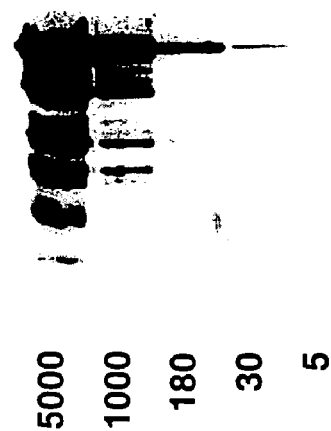

14. Western Blot using additional Ketene Dithioacetal Substrate. Western blot assays of β-galactosidase were conducted according Example 13 using detection reagents containing either compound 27 or compound 37 and an enhancer and peroxide. FIG. 6 demonstrates the detection of β-gal after 60 min with a 1 min exposure using compound 27 and an 1 min exposure after 8 min using compound 37.

15. Additional Ketene Dithioacetals. The following compounds were prepared.

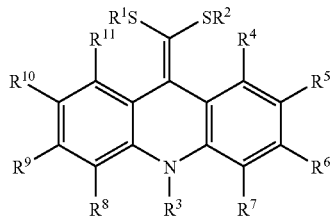

| Cmpd. | R⁴⁻¹¹ | R³ | R¹ | R² |
|---|---|---|---|---|
| 40 | — | $CH_2$-p-$C_6H_4OH$ | $CH_3$ | $CH_3$ |
| 41 | — | $CH_2Ph$ | $CH_2$-p-$C_6H_4Cl$ | $(CH_2)_3SO_3Na$ |
| 42 | — | Ph | $CH_2Ph$ | $(CH_2)_3SO_3Na$ |
| 43 | — | $CH_2Ph$ | $(CH_2)_3OPO_3Na_2$ | $(CH_2)_3OPO_3Na_2$ |
| 44 | — | $CH_2Ph$ | $(CH_2)_3OH$ | $(CH_2)_3OPO_3Na_2$ |
| 45 | — | Ph | —$CH_2CH(OH)CH_2$— | |
| 46 | — | Ph | —$CH_2CH(O(CH_2)_3SO_3Na)CH_2$— | |
| 47 | — | $CH_2Ph$ | —$CH_2CH(O(CH_2)_3SO_3Na)CH_2$— | |
| 48 | — | $CH_2Ph$ | —$CH_2CH(O(CH_2)_3OPO_3Na_2)CH_2$— | |
| 49 | — | $CH_2Ph$ | —$CH_2CH_2(OCH_2CH_2)_4$— | |
| 50 | — | $(CH_2)_3O(CH_2)_3SO_3Na$ | o-$C_6H_4$ | |
| 51 | — | $CH_3$ | o-$C_6H_4$ | |
| 52 | — | $CH_2Ph$ | $(CH_2)_3OH$ | $(CH_2)_3O(CH_2)_3SO_3Na$ |
| 53 | — | $CH_2Ph$ | $CH_3$ | $(CH_2)_3O(CH_2)_3SO_3Na$ |
| 54 | — | Ph | $CH_3$ | $(CH_2)_3S(CH_2)_3SO_3Na$ |
| 55 | — | $CH_2Ph$ | $CH_3$ | $(CH_2)_3OSO_3Na$ |
| 56 | — | Ph | $CH_3$ | $(CH_2)_3O(CH_2)_3SO_3Na$ |

Compound 51 was prepared as described in the aforementioned Akiba article.

16. Additional Synthesis and Characterization.

Compound 40: $^1$H NMR (CDCl$_3$): δ 2.28 (s, 6H), 4.74 (s, 1H), 5.21 (s, 2H), 6.76 (d, 2H), 6.87 (d, 2H), 7.00 (m, 4H), 7.12 (t, 2H), 7.85 (d, 2H).

Compound 41: $^1$H NMR (CDCl$_3$): δ 2.03 (p, 2H), 2.78 (t, 2H), 2.94 (t, 2H), 3.86 (s, 2H), 5.29 (s, 2H), 6.80-7.15 (m, 12H), 7.28 (m, 3H), 7.59 (d, 1H), 7.93 (d, 1H).

Compound 42: $^1$H NMR (CDCl$_3$): δ 1.82 (p, 2H), 2.60 (t, 2H), 2.75 (t, 2H), 3.83 (s, 2H), 6.29-6.36 (m, 2H), 6.80-6.85 (t, 1H), 6.90-7.03 (m, 3H), 7.12 (s, 5H), 7.22-7.25 (d, 2H), 7.48-7.63 (m, 4H), 7.78-7.80 (d, 1H).

Compound 43: $^1$H NMR (D$_2$O): δ 1.77 (p, 4H), 2.88 (t, 4H), 3.69 (q, 4H), 5.30 (s, 2H), 6.98 (d, 2H), 7.06 (m, 4H), 7.18-7.29 (m, 5H), 7.88 (d, 2H).

Compound 44: $^1$H NMR (CD$_3$OD): 1.70 (p, 2H), 1.88 (p, 2H), 2.78 (t, 2H), 2.92 (t, 2H), 3.15 (t, 2H), 3.85 (q, 2H), 5.29 (s, 2H), 6.90 (t, 2H), 6.98 (m, 2H), 7.08-7.26 (m, 7H), 7.74 (d, 1H), 7.95 (d, 1H).

Synthesis of Compound 45. To an LDA (30.8 mmol) solution in THF (250 mL) at −78° C. was added N-phenyl acridan (3.86 g, 15.0 mmol) in THF (20 mL). The resulting mixture was stirred at −78° C. for 1.5 hrs. CS$_2$ (0.99 mL, 16.5 mmol) was then added. After 45 min. at −78° C., the reaction was allowed to warm up to room temperature and stirred further for 30 min. before [2-(1,3-dibromo)propoxy]-tert-butyldimethylsilane (5.23 g, 15.8 mmol) was added in THF (130 mL). After overnight stirring, the solvent was removed and the residue was subject to column chromatography (silica gel, hexanes/CH$_2$Cl$_2$: 1/2.5). Compound 45 (6.15 g) was obtained (81% yield). Deprotection of the siloxy group with TBAF furnished 45 in 85% yield. $^1$H NMR (CDCl$_3$): δ 2.76 (dd, 2H), 2.82 (br, 1H), 3.19 (dd, 2H), 4.22 (m, 1H), 6.76 (d, 2H), 7.01-7.13 (m, 4H), 7.38 (d, 2H), 7.55 (t, 1H), 7.62-7.72 (m, 4H).

Synthesis of Compound 46. To a solution of 45 (1.00 g, 2.57 mmol) in DMF (10 mL) under argon was added sodium hydride (0.108 g, 60% in mineral oil, 2.70 mmol). After about 1 hr and 20 min, a clear solution was resulted. 3-Propanesultone was then added and the mixture stirred at room temperature for 60 hrs. The reaction mixture was concentrated to a volume of about 3 mL by removing DMF in vacuum. Acetone (7 mL) was added to precipitate the product. The mixture was stirred for 20 min. before the solid was collected by filtration. The solid was washed with acetone (3×5 mL) and dried to give 1.12 g of the crude product. Recrystallization with water and isopropanol gave 0.80 g of pure 46 as a yellowish solid (58% yield). $^1$H NMR (CDCl$_3$): δ 2.16 (p, 2H), 2.90 (t, 4H), 6.44 (d, 2H), 6.99-7.10 (m, 4H), 7.38 (d, 2H), 7.54 (m, 1H), 7.64 (m, 2H), 7.71 (dd, 2H).

Compound 47. H$^1$ NMR (CD$_3$OD): δ 0.03 (2H, m), 2.87 (4H, m), 3.08 (2H, m), 3.62 (2H, t, J=6.5 Hz), 4.00 (1H, m), 5.26 (2H, s), 6.81 (2H, d, J=8.2 Hz), 6.94 (2H, m), 7.07 (4H, m), 7.21-7.29 (3H, m), 7.65 (2H, d, J=7.5 Hz).

Compound 48. H$^1$ NMR (CD$_3$OD): δ 1.85 (2H, m), 2.84 (2H, m), 3.06 (2H, m), 3.63 (2H, t, J=6.7 Hz), 3.87 (2H, m), 3.99 (1H, m), 5.21 (2H, s), 6.78 (2H, d, J=8.1 Hz), 6.93 (2H, m), 7.05 (4H, m), 7.19-7.27 (3H, m), 7.64 (2H, d, J=7.2 Hz). P$^{31}$ NMR (CD$_3$OD): d 10.27 (s)

Compound 49. H$^1$ NMR (CDCl$_3$): δ 2.92 (4H, t, J=7.1 Hz), 3.51-3.63 (16H, m), 5.27 (2H, s), 6.85 (2H, d, J=8.7 Hz), 7.02 (2H, m), 7.11-7.16 (4H, m), 7.25-7.30 (3H, m), 7.93 (2H, d, J=7.5 Hz).

Compound 50. H$^1$ NMR (CD$_3$OD): δ 2.03 (m, 4H), 2.85 (t, 2H), 3.48 (m, 4H), 4.14 (t, 2H), 7.02-7.10 (m, 4H), 7.18-7.33 (m, 6H), 7.45 (d, 2H).

17. Comparison of Signal Intensity. The maximum signal produced by each of compounds 40-51 was compared by reacting a 100 μL aliquot of reagent compositions comprising 0.025 M tris buffer, pH 8, 2.5 mM urea peroxide, 4 mM p-hydroxycinnamic acid, 0.5 mM EDTA, 0.1% Tween 20, and either 1 mM, 0.3 mM, 0.15 mM or 0.05 mM of the test compound with 3.5×10$^{-16}$ moles of HRP. Each reagent reached maximum light intensity in 1-3 minutes.

| Compound | Formulation | Signal/Background |
|---|---|---|
| 40 | 1.0 | 4011 |
| 41 | 1.0 | 14000 |
| 42 | 1.0 | 9100 |
| 43 | 1.0 | 1121 |
| 44 | 1.0 | 5810 |
| 45 | 0.3 | 2102 |
| 46 | 1.0 | 13000 |
| 47 | 1.0 | 7228 |
| 48 | 1.0 | 4219 |
| 49 | 0.05 | 4853 |
| 50 | 0.3 | 1651 |
| 51 | 0.05 | 4264 |
| 52 | 0.15 | 5840 |
| 53 | 0.15 | 5742 |
| 54 | 0.15 | 2502 |
| 55 | 0.3 | 5408 |

Compounds 49 and 51 were very poorly soluble in the aqueous formulation.

Figure 7:
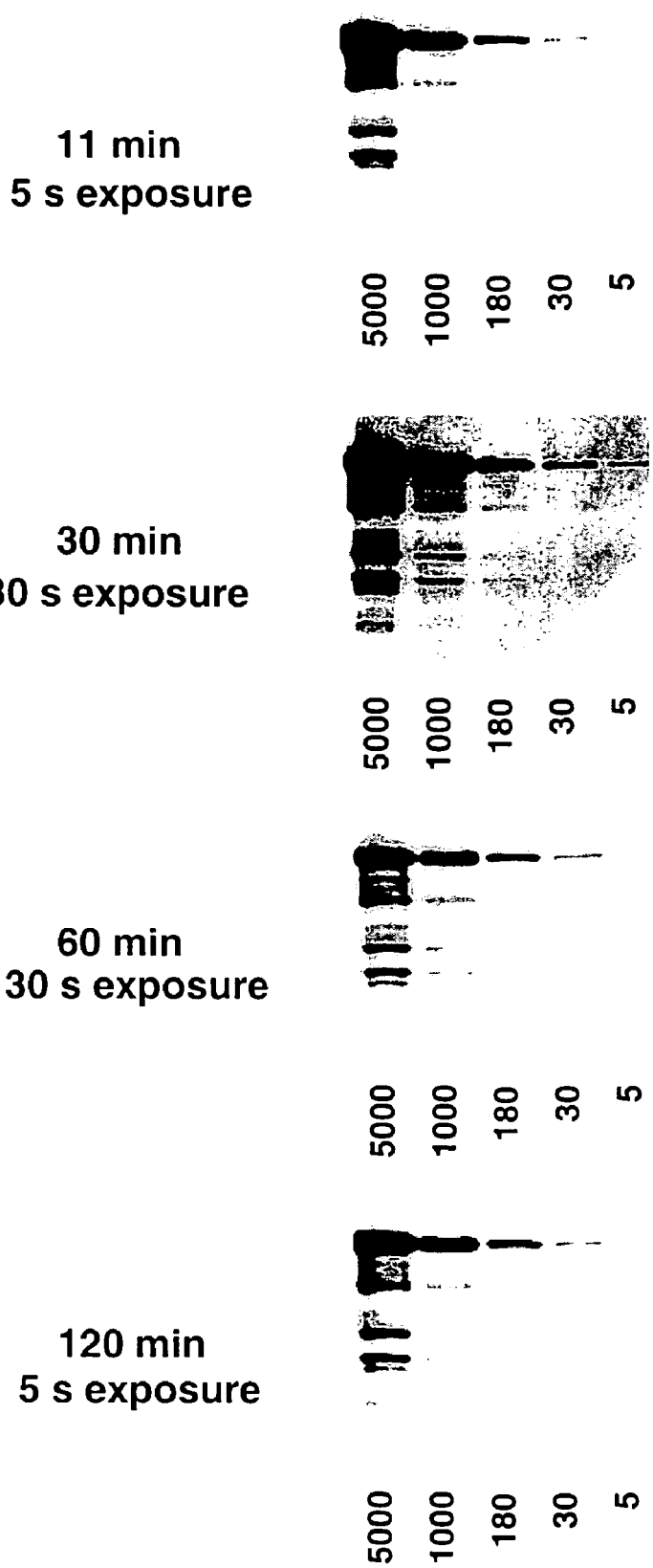
FIG. 7 depicts images of x-ray films from a western blot assay of β-galactosidase via an HRP-labeled antibody on a nitrocellulose membrane with a chemiluminescent reagent composition containing compound 46. Dilutions of β-galactosidase containing 5000, 1000, 180, 30 and 5 pg, respectively, of protein were easily detected over a two hour period as shown.

18. Western Blot using Ketene Dithioacetal Substrate 46. Western blot assays of β-galactosidase were conducted according to Example 13 but using nitrocellulose membrane and a detection reagent comprising 0.025 M tris buffer, pH 8.0, 2.5 mM urea peroxide, 4 mM p-hydroxycinnamic acid, 0.5 mM EDTA, 0.1% Tween 20, and 1 mM compound 46. FIG. 7 demonstrates the rapid and convenient detection of β-gal with excellent sensitivity at various time points up to 120 min.

19. Additional Compounds.

Compound 52. 1H NMR (CD$_3$OD): δ 1.59-1.70 (m, 4H), 1.95 (m, 2H), 2.72-2.83 (m, 6H), 3.18 (t, 2H), 3.34 (t, 2H), 3.45 (t, 2H), 5.29 (s, 2H), 6.91-7.02 (m, 4H), 7.09-7.25 (m, 7H), 7.82 (d, 1H), 7.88 (d, 1H) ppm.

Compound 53. 1H NMR (CD$_3$OD): δ 1.54 (p, 2H), 1.92 (m, 2H), 2.21 (s, 3H), 2.70-2.82 (m, 4H), 3.10 (t, 2H), 3.29 (t, 2H), 5.30 (S, 2H), 6.90-7.02 (m, 4H), 7.08-7.26 (m, 7H), 7.78 (d, 1H), 7.89 (d, 1H) ppm.

Compound 56. 1H NMR (CD$_3$OD): δ 1.60 (p, 2H), 1.93 (m, 2H), 2.27 (s, 3H), 2.71-2.82 (m, 4H), 3.14 (t, 2H), 3.32 (t, 2H), 6.43 (t, 2H), 6.98-7.10 (m, 4H), 7.32 (d, 2H), 7.57 (m, 1H), 7.69 (m, 2H), 7.82 (d, 1H), 7.92 (d, 1H) ppm.

20. Synthesis of Compound 54. A mixture of compound 16 (0.500 g, 0.97 mmol) and potassium thioacetate (0.166 g, 1.45 mmol) in DMF (10 mL) was stirred under argon at RT overnight. After removal of DMF in vacuum, the residue was taken up with CH$_2$Cl$_2$ and passed through a silica gel pad. Removal of solvent gave 0.46 g of A as a foam-like solid.

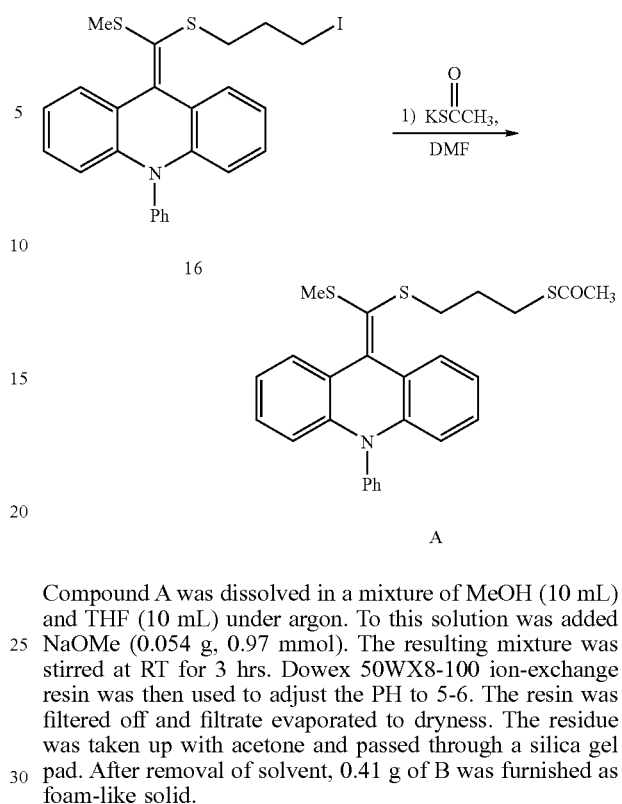

Compound A was dissolved in a mixture of MeOH (10 mL) and THF (10 mL) under argon. To this solution was added NaOMe (0.054 g, 0.97 mmol). The resulting mixture was stirred at RT for 3 hrs. Dowex 50WX8-100 ion-exchange resin was then used to adjust the PH to 5-6. The resin was filtered off and filtrate evaporated to dryness. The residue was taken up with acetone and passed through a silica gel pad. After removal of solvent, 0.41 g of B was furnished as foam-like solid.

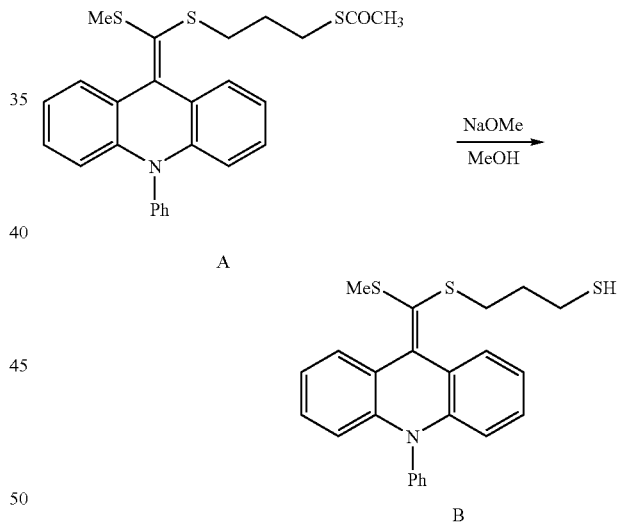

B: $^1$H NMR (CDCl$_3$): d 1.21 (t, 1H), 1.72 (p, 2H), 2.30 (m, 2H), 2.35 (s, 3H), 2.80 (t, 2H), 6.49 (t, 2H), 7.02-7.14 (m, 4H), 7.38 (d, 2H), 7.55 (t, 1H), 7.65 (m, 2H), 7.88 (d, 1H), 7.95 (d, 1H) ppm.

Compound B was converted to Compound 54 by reaction with propanesultone and NaH in DMF as described above. $^1$H NMR (CD$_3$OD): δ 1.59 (p, 2H), 1.92 (p, 2H), 2.22 (t, 2H), 2.27 (s, 3H), 2.45 (t, 2H), 2.73-2.85 (m, 4H), 6.43 (dd, 2H), 6.98-7.10 (m, 4H), 7.35 (d, 2H), 7.58 (m, 1H), 7.67 (m, 2H), 7.80 (d, 1H), 7.92 (d, 1H) ppm.

21. Synthesis of Compound 55. A mixture of the dithioester (1.00 g, 2.77 mmol) and NaH (2.77 mmol) in DMF was stirred under argon for 1 hr. 1,3-Propanediol cyclic sulfate was then added and the resulting mixture stirred at RT overnight. After removal of DMF, the residue was washed with acetone/ether (1:3) and recrystallized with MeOH/2- propanol to give 1.40 g of 55 (yield 96%). ¹H NMR (300 MHz, CD₃OD) δ 1.69 (p, 2H), 2.21 (s, 3H), 2.76 (t, 2H), 3.83 (t, 2H), 5.31 (s, 2H), 6.90 (m, 2H), 6.99 (m, 2H), 7.10 (m, 4H), 7.24 (m, 3H), 7.83-7.88 (dd, 2H) ppm.

Figure 8:
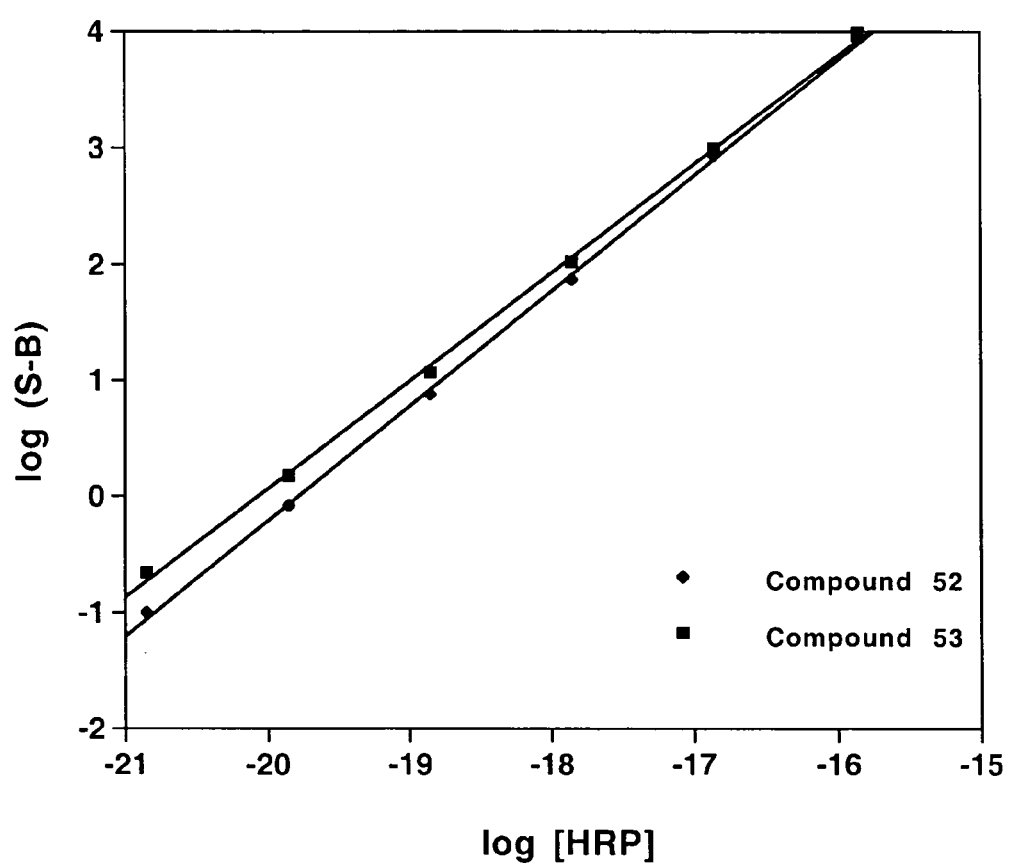
FIG. 8 is a graph relating the amount of HRP to the chemiluminescence intensity emitted by 100 μL of a reagent described in Example 22 containing either compound 52 or 53 triggered at room temperature.

22. Chemiluminescent Detection of HRP with Compounds 52 and 53. Reagent compositions comprising 0.025 M tris buffer, pH 8.0, 2.5 mM urea peroxide, 4 mM p-hydroxycinnamic acid, 0.5 mM EDTA, 0.1% Tween 20 and 3×10⁻⁴ M compound 52 or 53 were tested for production of chemiluminescence by reacting triplicate 100 μL aliquots with 10 μL of HRP in the range 1.4×10⁻¹⁶ to 1.4×10⁻²¹ moles. Light production ensued upon mixing and reached maximum intensity rapidly. The relation between peak chemiluminescence intensity and amount of enzyme is depicted in FIG. 8.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A compound selected from the group

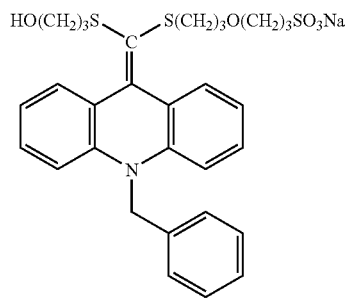

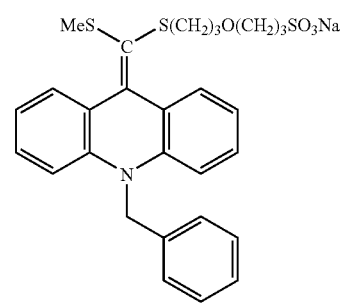

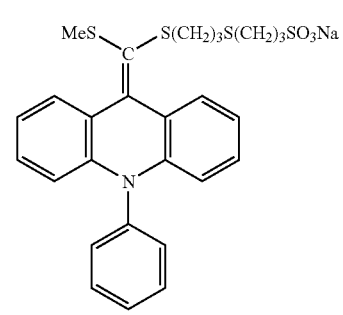

-continued

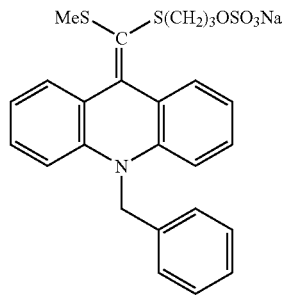

and

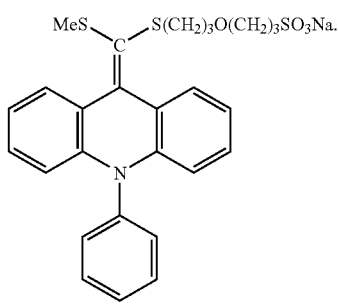

2. The compound of claim 1 which has the formula

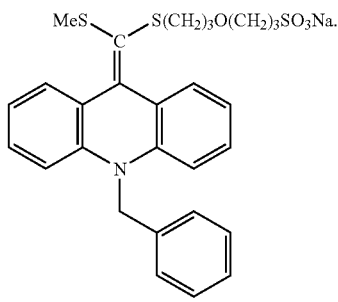

3. A compound selected from the group

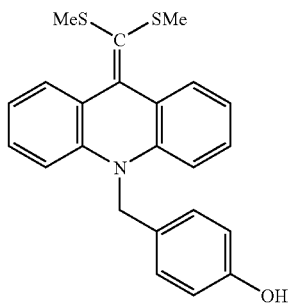

-continued
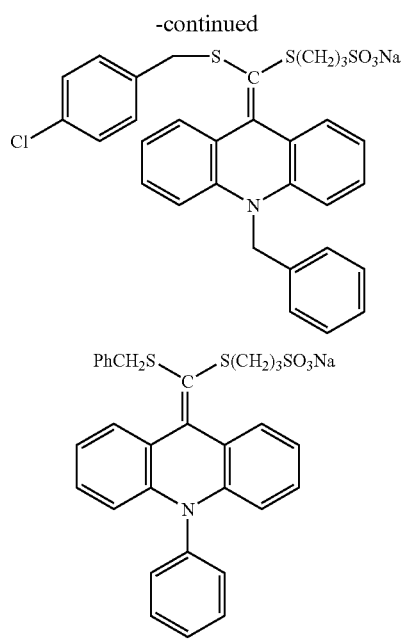
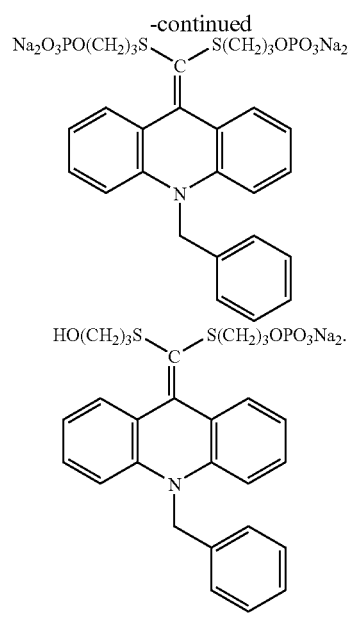
and
* * * * *